US009782450B2

(12) United States Patent
Majeed et al.

(10) Patent No.: US 9,782,450 B2
(45) Date of Patent: *Oct. 10, 2017

(54) COMPOSITION COMPRISING SCIRPUSIN A AND SCIRPUSIN B AND ANTI-OBESITY POTENTIAL THEREOF

(71) Applicant: SAMI LABS LIMITED, Bangalore (IN)

(72) Inventors: Muhammed Majeed, Edison, NJ (US); Kalyanam Nagabhushanam, East Windsor, NJ (US); Douglas Kalman, Weston, FL (US); Beena Bhat, Bangalore (IN); Priti Vaidyanathan, Bangalore (IN); Sarang Bani, Bangalore (IN); Anjali Pandey, Bangalore (IN); Suresh Karri, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/705,111

(22) Filed: May 6, 2015

(65) Prior Publication Data

US 2015/0238438 A1 Aug. 27, 2015

Related U.S. Application Data

(63) Continuation-in-part of application No. 13/944,634, filed on Jul. 17, 2013, now Pat. No. 9,387,193.

(60) Provisional application No. 61/672,849, filed on Jul. 18, 2012.

(51) Int. Cl.
*A61K 36/8905* (2006.01)
*A61K 31/343* (2006.01)
*A61K 31/015* (2006.01)

(52) U.S. Cl.
CPC ........ *A61K 36/8905* (2013.01); *A61K 31/015* (2013.01); *A61K 31/343* (2013.01)

(58) Field of Classification Search
CPC ............ A61K 31/015; A61K 31/343; A61K 36/8905
See application file for complete search history.

(56) References Cited

U.S. PATENT DOCUMENTS

2012/0128808 A1* 5/2012 Gokaraju ............... A61K 36/60
424/777

* cited by examiner

*Primary Examiner* — Sarah Pihonak
*Assistant Examiner* — Jason A Deck
(74) *Attorney, Agent, or Firm* — Oliff PLC

(57) ABSTRACT

Disclosed are methods of managing obesity and hypercholesterolemia using a composition of matter comprising the ethyl acetate fraction of the extract of *Cyperus rotundus* rhizomes standardized to contain 5% of total stilbenes.

2 Claims, 19 Drawing Sheets

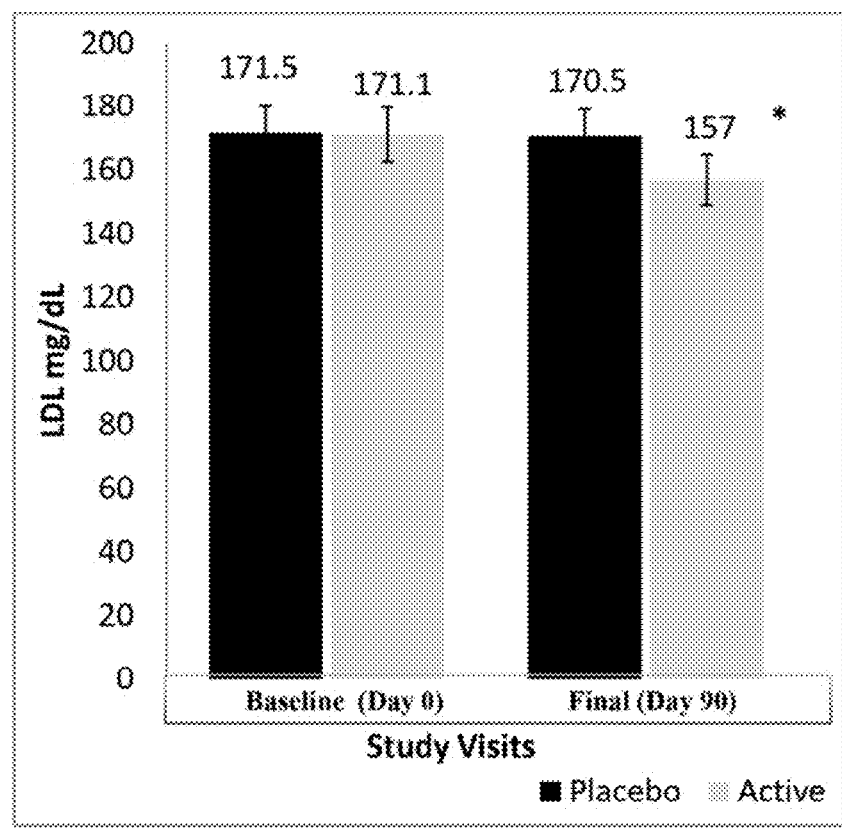

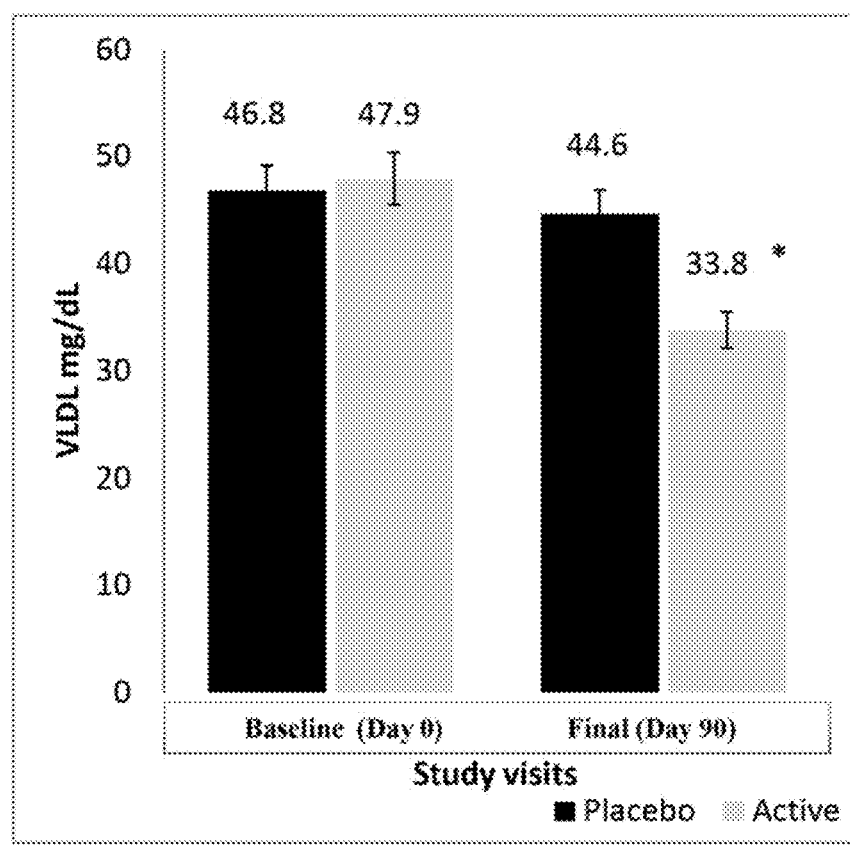

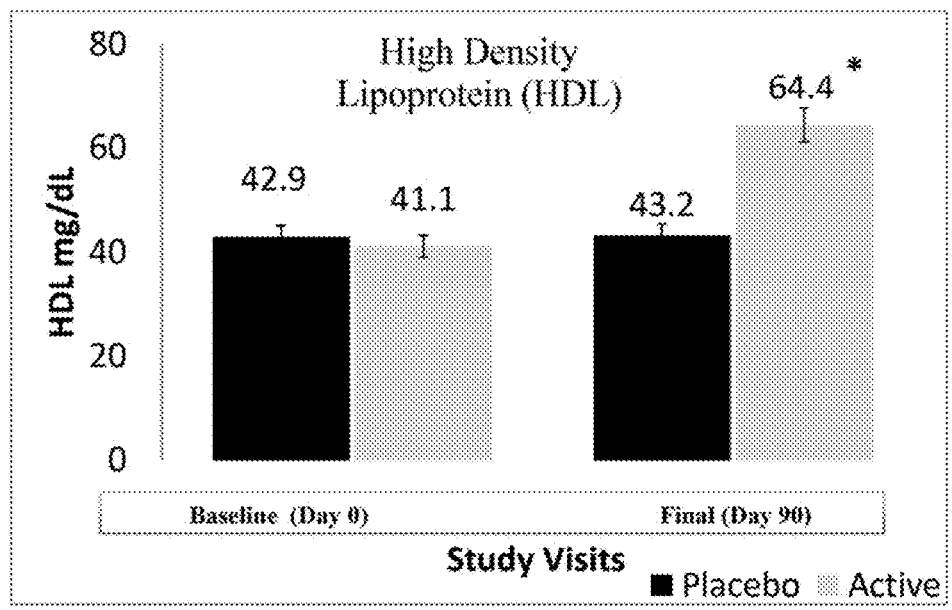

COMPOSITION COMPRISING SCIRPUSIN A AND SCIRPUSIN B AND ANTI-OBESITY POTENTIAL THEREOF

CROSS REFERENCE TO RELATED APPLICATIONS

The present invention is a continuation-in-part patent application from U.S. Ser. No. 13/944,634 filed Jul. 17, 2013 which in turn is a non-provisional filing of provisional patent application 61/672,849 filed Jul. 18, 2012. U.S. Ser. No. 13/944,634 is incorporated herein below for reference in its entirety.

BACKGROUND OF THE INVENTION

Field of the Invention

The invention in general pertains to compositions for adipogenesis inhibition. More specifically, the present invention discloses a composition comprising scirpusin A and scirpusin B and anti-adipogenesis/anti-obesity potential thereof.

Description of Prior Art

Scirpusin A as a hydroxystilbene dimer from Xinjiang wine grape has been previously reported by Kong Q et al in J Sci Food Agric. 2010 Apr. 15; 90(5):823-8. Scirpusin A has been noted for its amyloid-beta-peptide aggregation inhibitory activity (Riviere C et al (2010)), singlet oxygen quenching and DNA protective activity (Kong Q et al (2010)) and beta-secretase inhibitory activity (Jeon S Y et al (2007)).

Scirpusin B is a well established vaso-relaxing dinner of piceatannol and has been obtained in large amounts from passion fruit (Sano S et al, "Identification of the strong vaso-relaxing substance scirpusin B a dimer of piceatannol, from passion fruit (*Passiflora edulis*) seeds, J Agric Food Chem. 2011 Jun. 8; 59(11):6209-13. Scirpusin B is also noted for its mild GSH activity (Maruki-Uchida H et al (2013)) and anti-HIV properties (Yang G X et al (2005)).

It has been previously reported that hexane extract of *Cyperus rotundus* rhizome extracts exhibit anti-obesity properties, (Administration of *Cyperus rotundus* rhizomes extract prevents Weight Gain in Obese Zucker rats. Lemaure of al 2007. Phytother Res. 21: 724-730.). The hexane fraction has been characterized to contain α-Cypernone, Rotundene, β-selinene, Calamenene. Cyperene, d-cadinene, Cyperotundone, Cadalene, Patchoulenone, Nootkatene, Sugeonol, g-calacorene, Kobusone, Cyperol, Isokobusone and Epi-a-selinene (Yadav et al, International Journal of Pharmaceutical and Clinical Research 2010; 2(1): 20-22). But the present invention discloses anti-obesity activity in ethyl acetate fraction of *Cyperus rotundus*. This ethyl acetate fraction does not contain any of the many constituents of the hexane fraction. The present ethyl acetate fraction contains stilbenoid derived compounds, a class of compounds not reported to be courting *Cyperus rotundas* by any investigator thus far. Hence it is the unique combination of the unexpected discovery of the occurrence of stilbenoid derived compounds and further, their anti-obesity action. It is also a surprising finding that following the bioactivity guided fractionation of the rhizomes from *Cyperus rotundus*, a sub fraction of ethyl acetate layer was characterized by the concentrated presence of two piceatannol dimers scirpusin A and scirpusin B which showed excellent anti-adipogenic effect in comparison to another sub fraction that was concentrated with piceatannol along with dimers scirpusin A and scirpusin B. Thus the inventors of the present invention demonstrate for the first time the presence of scirpusin A and scirpusin B in the ethyl acetate fraction of the rhizomes *Cyperus rotundas* and anti-adipogenesis/anti-obesity potential thereof.

It is thus the principle objective of the present invention to disclose a composition scirpusin A and scirpusin Band anti-adipogenesis/anti-obesity potential thereof.

It is another objective of the present invention to disclose a method of inhibiting adipogenesis in mammalian cells using a composition comprising scirpusin A and scirpusin B.

It is yet another objective of the present invention to disclose a method of managing obesity in mammals using a composition comprising scirpusin A and scirpusin B.

It is a further objective of the present invention disclose a method of obtaining compositions comprising A scirpusin A and scirpusin B and B. Piceatannol and its dimers scirpusin A and scirpusin B through bioactivity guided fractionation of the rhizomes of *Cyperus rotundus*.

The present invention fulfils the aforesaid objectives and provides further related advantages.

SUMMARY OF THE INVENTION

The present invention discloses compositions comprising scirpusin A and scirpusin B and anti-adipogenesis/anti-obesity potential thereof. The invention also discloses a method of managing obesity in mammals using a composition comprising scirpusin A and scirpusin B. The present invention further discloses a method of obtaining compositions comprising A. scirpusin A and scirpusin B and B. piceatannol and its dimers scirpusin A and scirpusin B through bioactivity guided fractionation of the rhizomes of *Cyperus rotundus*. Other features and advantages of the present invention will become apparent from the following more detailed description, taken in conjunction with the accompanying images, which illustrate, by way of example, the principle of the invention.

DETAILED DESCRIPTION OF THE DRAWINGS

Figure 6:
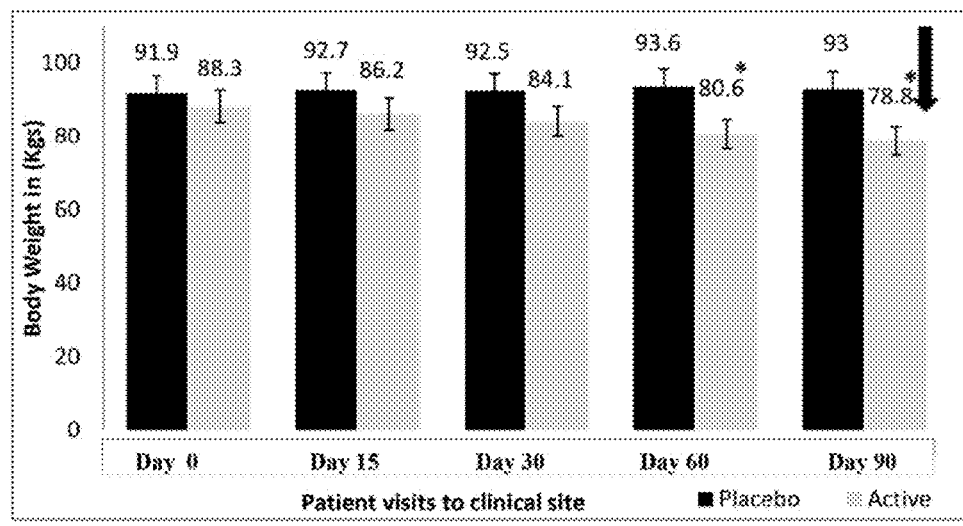
Figure 6A:
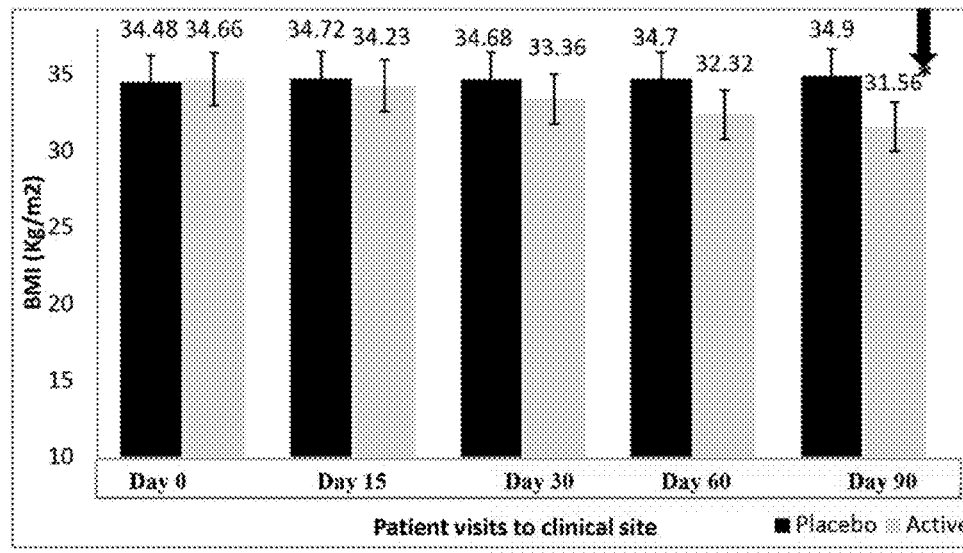
Figure 6B:
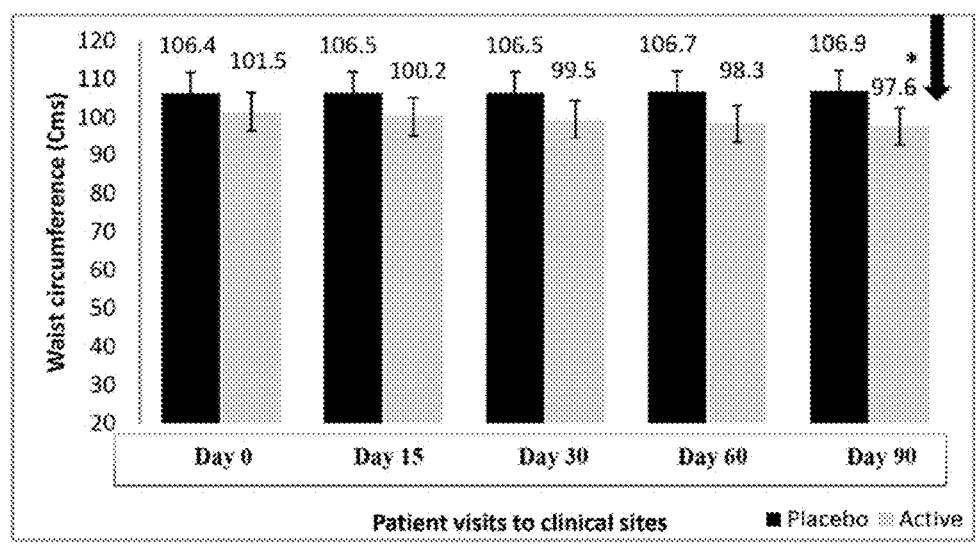

FIG. 6 shows the graphical reduction in body weight in obese humans administered the ethyl acetate fraction of the extract of *Cyperus rolundus* rhizomes standardised to 5% total stilbenes. FIG. 6a shows the graphical reduction in body mass index in obese humans administered the ethyl acetate fraction of the extract of *Cyperus rotundus* rhizomes standardised to 5% of total stilbenes. FIG. 6b shows the graphical reduction in waist circumference in obese humans administered the ethyl acetate fraction of the extract of *Cyperus rotundus* rhizomes standardised to 5% of total stilbenes.

Figure 7:
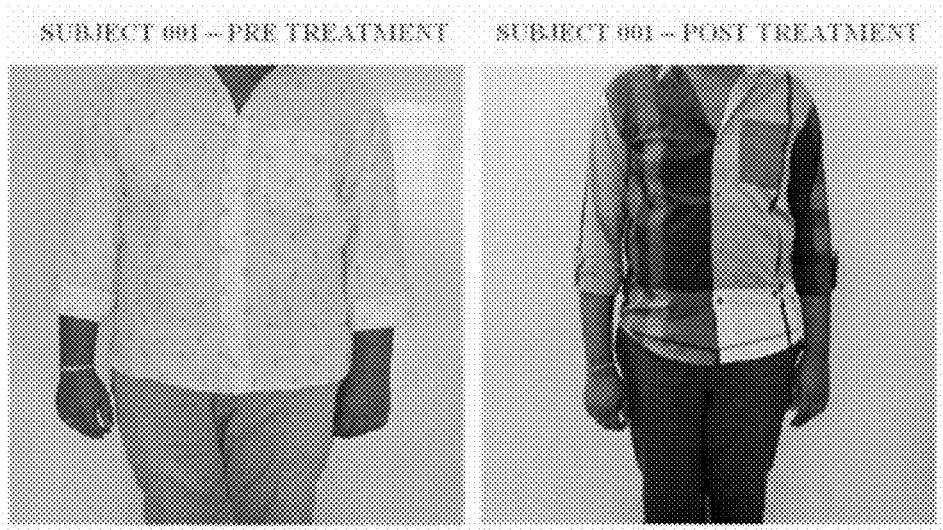

FIG. 7 shows the photographs of waist circumference reduction in obese humans (males) administered the ethyl acetate fraction of the extract of *Cyperus rotundus* rhizomes standardised to 5% of total stilbenes.

Figure 8A:
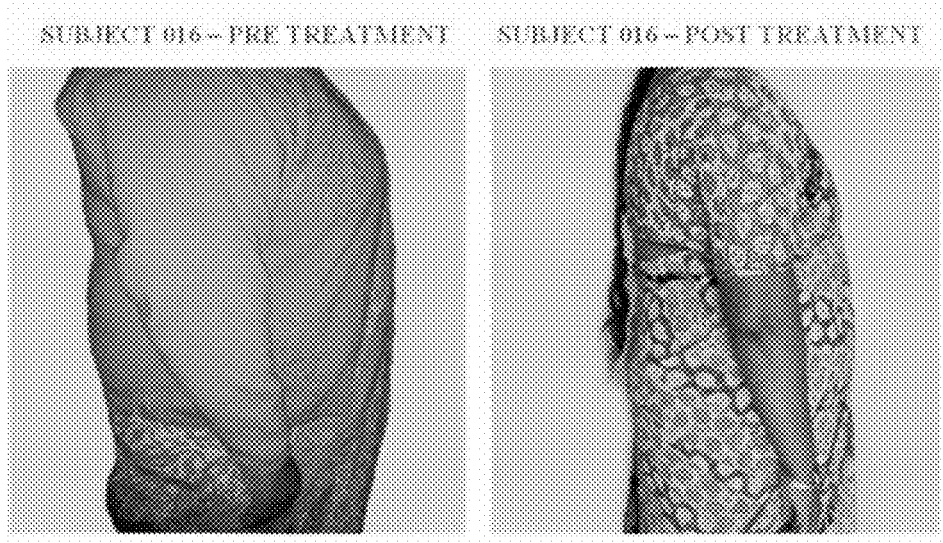
Figure 8B:
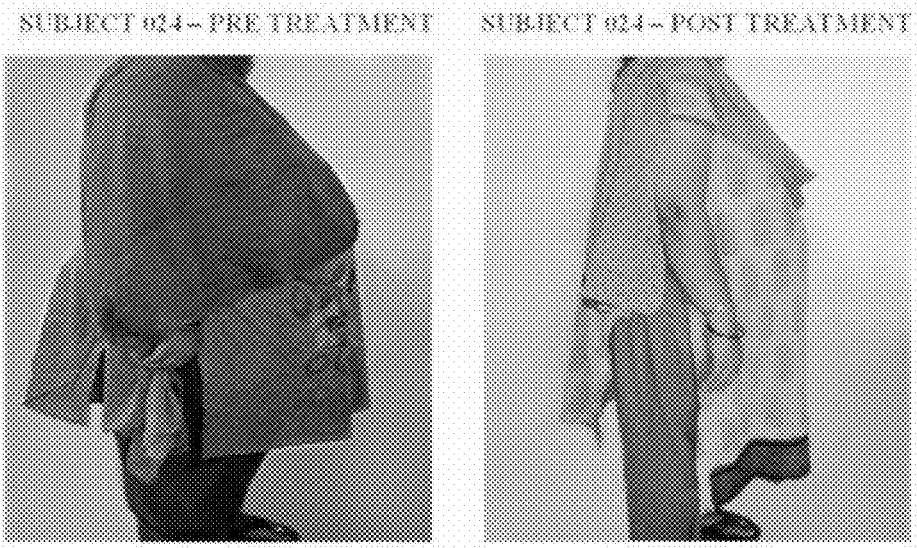
Figure 8C:
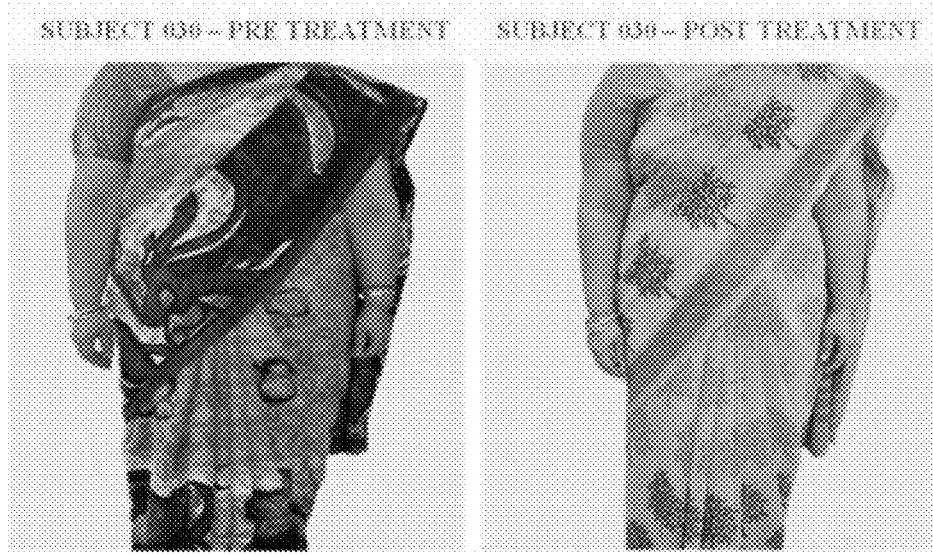
Figure 9A:
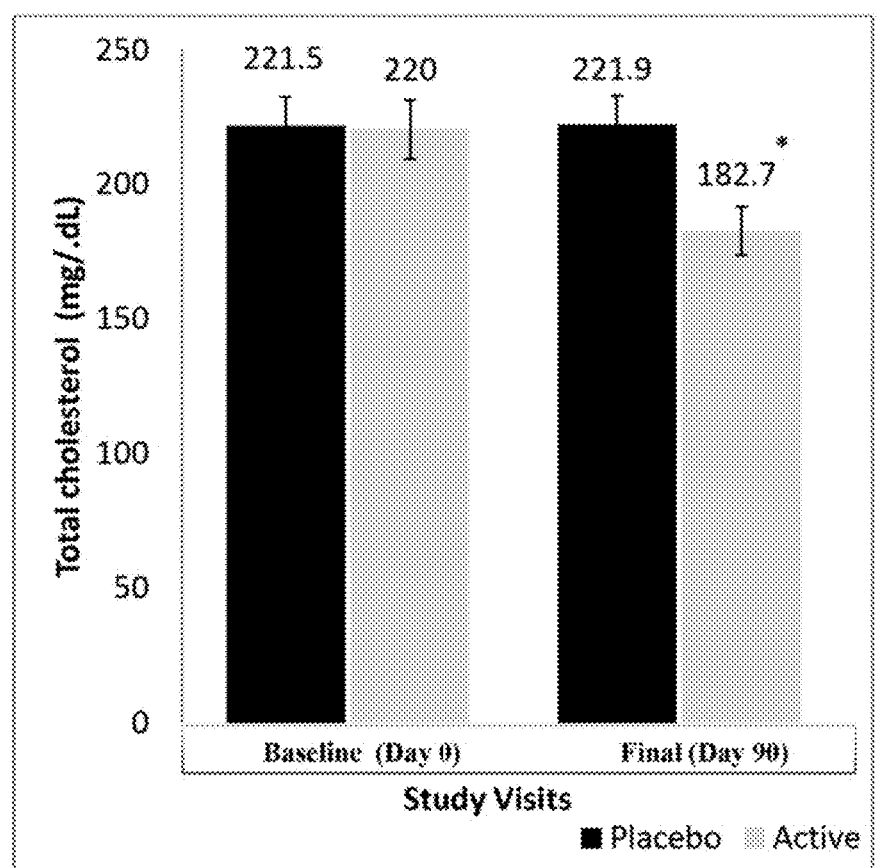
Figure 9B:
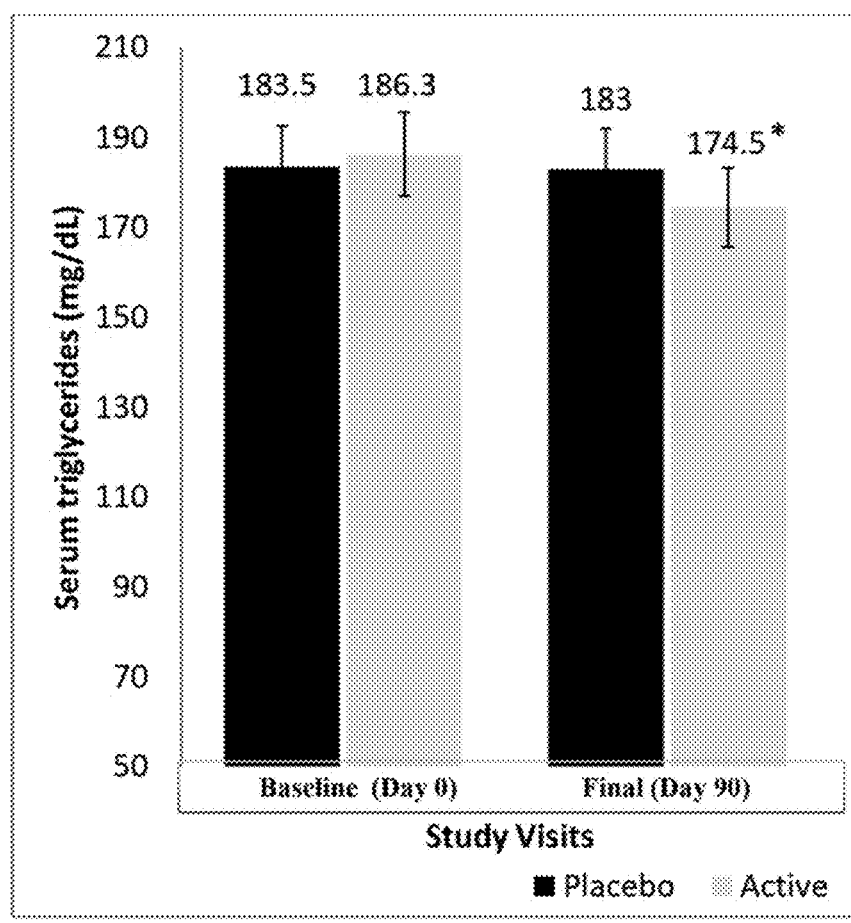

FIGS. 8a, 8b and 8c shows the photographs of waist circumference reduction in obese humans (females) administered the ethyl acetate fraction of the extract of *Cyperus rotundus* rhizomes standardised to 5% of total stilbenes.

FIGS. 9a, 9b, 9c, 9d and 9e show the changes in systemic lipids in obese humans administered the ethyl acetate fraction of the extract of *Cyperus rotundus* rhizomes standardised to 5% of total stilbenes.

DESCRIPTION OF THE MOST PREFERRED EMBODIMENT

In the most preferred embodiment the present invention relates to anti adipogenic obesity composition comprising scirpusin A and scirpusin B represented by STR#1 and STR#2 respectively.

In another most preferred embodiment, the present invention relates to a method of inhibiting adipogenesis in mammalian cells, said method comprising step of bringing to contact adipogenic mammalian cells with a composition comprising scirpusin A and scirpusin B represented by STR#1 and STR#2 respectively.

In another most preferred embodiment, the present invention relates to the method of therapeutically inhibiting obesity caused by adipogenesis in mammals, said method comprising step of dietary supplementation of a composition comprising scirpusin A and scirpusin B represented by STR#1 and STR#2 respectively to a mammal in need of said therapeutic inhibition.

In another most preferred embodiment, the present invention relates to the use of a composition comprising scirpusin A and scirpusin B represented by STR#1 and STR#2 for inhibiting adipogenesis in mammalian cells.

In an alternate embodiment, the present invention also relates to a process for the bioactivity guided fractionation of the rhizomes of *Cyperus rotundus* to obtain anti-adipogenic/anti-obesity compositions comprising A. scirpusin A and scirpusin B represented by STR#1 and STR#2 and B. piceatannol and its dimers scirpusin A and scirpusin B represented by STR#1 and STR#2 respectively, said process comprising the steps of:

1) Drying the rhizomes of *Cyperus rotundus* and pulverizing the same to form a coarse powder;
2) Extracting the powder of step 1 with 3 volumes of hexane followed by heating, reflux for
3) 3 hours and filtering to obtain the hexane soluble fraction and spent material;
4) Extracting the spent material of step 2 with 3 volumes of methanol followed by heating, reflux for 3 hours and filtering to obtain the methanol soluble active fraction and spent material;
5) Solubilising the methanol soluble active fraction of step 3 in aqueous methanol and successively partitioning with chloroform ($CHCl_3$). Ethyl acetate (EtOAc) and methanol to obtain the chloroform layer, ethyl acetate layer and the aqueous methanol layer respectively;
6) Subjecting the chloroform layer, ethyl acetate layer and the aqueous methanol layer to further bioactivity guided fractionation, wherein the bioactivity parameter is the ability of the chloroform layer, ethyl acetate layer and the aqueous methanol layer to inhibit adipogenesis in 3T3-L1 mouse adipocytes (mammalian adipocytes);
7) Calculating the $IC_{50}$, (µ/ml) values for adipogenesis inhibition exemplified by chloroform layer, ethyl acetate layer and the aqueous methanol layer (0, 9.39 and 66.42 respectively);
8) Fractionation of the ethyl acetate layer using column fractionation to identify the bioactivity (adipogenesis inhibition) biomarker, said fractionation includes the step where fractions are eluted with increasing polarity of methanol chloroform to yield sub-fractions of the ethyl acetate layer (fraction);
9) Subjecting the sub fractions of step 7 for bioactivity (anti-adipogenesis) analysis;
10) Identifying the most bioactive sub fractions of step 8 and subjecting the same to LC-MS analysis to identify the bioactive principles scirpusin A and scirpusin B; and
11) Subjecting sub fractions of step 7 through the preparative HPLC to obtain purified dimer and subjecting the same to High Resolution Mass Spectroscopy (HRMS), liquid chromatography-mass spectrometry (LC-MS/MS) and Nuclear Magnetic Resonance Spectroscopy (NMR) to confirm the mass and structures of scirpusin bioactive principles.

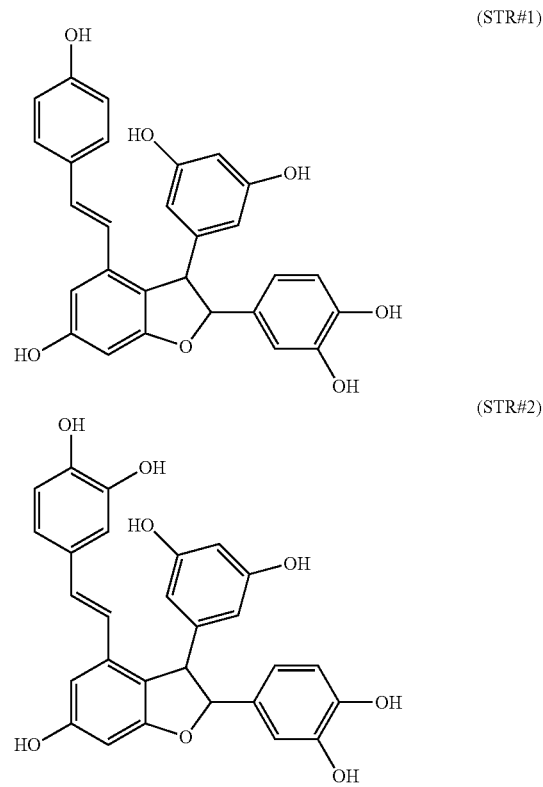

The present inventors investigated the hexane extract referred in step 2 preceding and found that Scirpusin A & Scirpusin B were not present. Hence hexane extract in step 1 is constitutionally different from ethyl acetate fraction detailed in step 7. Thus the ethyl acetate extract of *Cyperus rotundus* is quite different from the hexane extract that was the subject of investigation in Lemaure et al. 2007. Phytother Res. 21: 724-730.

The following sections of this specification consist of illustrative examples of the most preferred embodiments of the present invention.

Figure 1:
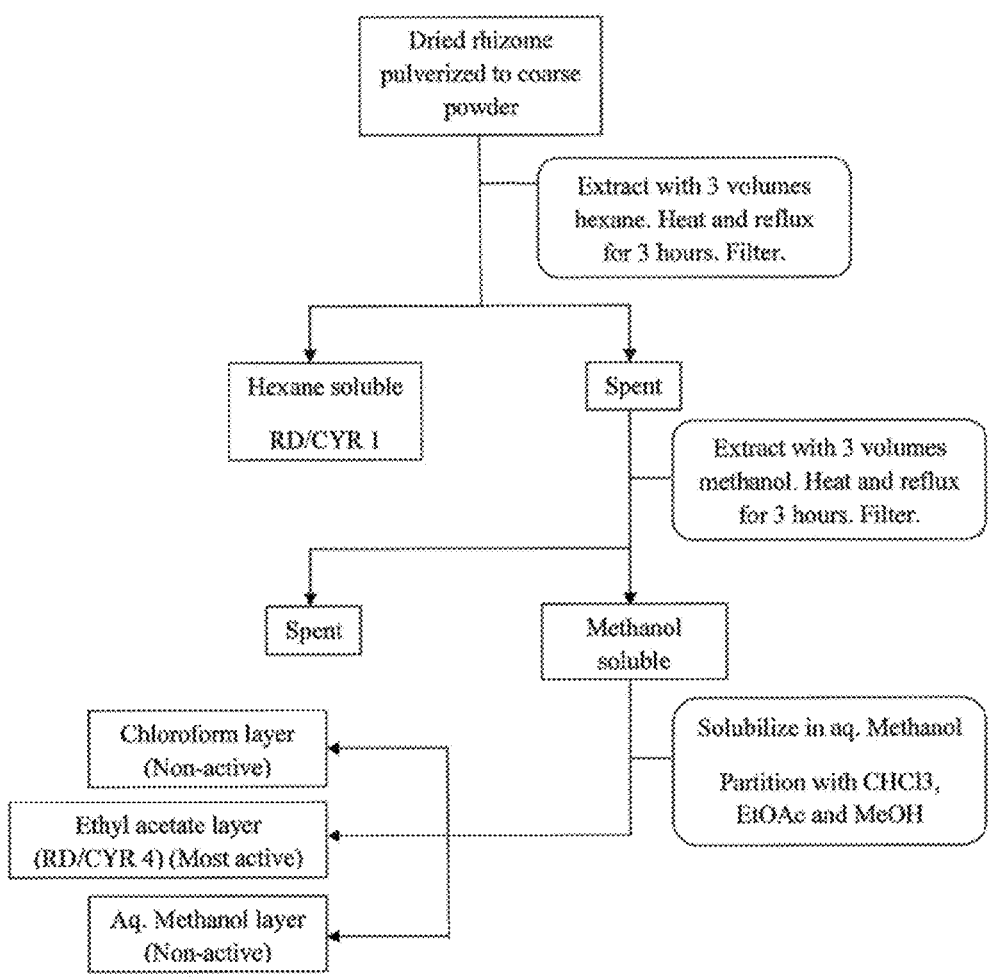
FIG. 1 shows a flowchart outlining the steps of extracting active principles from the rhizomes of *Cyperus rotundus*.

Example 1: Bioactivity Guided Fractionation of the Rhizomes of *Cyperus rotundus* (FIG. 1)

Methodology:

Dried rhizomes of *Cyperus rotundus* were pulverized to form a coarse powder. The pulverized powder was then extracted with 3 volumes of hexane followed by heating, reflux for 3 hours and filtering to obtain the hexane soluble fraction and spent material. The spent material is further extracted with 3 volumes of methanol followed by heating, reflux for 3 hours and filtering to obtain the methanol soluble active fraction and spent material. The methanol soluble fraction is solubilised in aqueous methanol and successively partitioned with chloroform ($CHCl_3$). Ethyl acetate (EtOAc) and methanol to obtain the chloroform layer, ethyl acetate layer and the aqueous methanol layer respectively. The chloroform layer, ethyl acetate layer and the aqueous methanol layer are subjected to further bioactivity guided fractionation, wherein the bioactivity parameter was the ability of the chloroform layer, ethyl acetate layer and the aqueous methanol layer to inhibit adipogenesis in 3T3-L1 mouse adipocytes (mammalian adipocytes). The steps of the Oil Red O staining technique as adapted from Salazar Olivo et al (1995), Wu Z et al (1998). Fu M et al (2005) to study extent of adipogenesis inhibition is explained in EXAMPLE 1A herein below. The results are mentioned in Table A.

Example 1A

Terminal differentiation of adipocytes is accompanied by the accumulation of great amounts of lipids in large cytoplasmic vesicles. A common assay to measure adipocyte differentiation in cell culture is with the dye Oil Red-O (ORO). ORO is a lipid-soluble bright red dye which is a reliable indicator of adipocyte differentiation.

Principle: Oil Red O (Solvent Red 27, Sudan Red 5B, C.I. 26125, and C26H24N40) is a lysochrome (fat-soluble dye) diazo dye used for staining of neutral triglycerides and lipids on frozen sections and some lipoproteins on paraffin sections. It has the appearance of a red powder with maximum absorption at 518(359) nm. Oil Red O is one of the dyes used for Sudan staining. Similar dyes include Sudan III, Sudan IV, and Sudan Black B. The staining has to be performed on fresh samples, as alcohol fixation removes the lipids. Oil Red O largely replaced Sudan III and Sudan IV, as it provides much deeper red colour and the stains are therefore much easier to see. Oil red O is an oil soluble dye. Oil soluble dyes exhibit greater solubility of the dye in lipoid substances in the tissues/cells, than in the usual hydro alcoholic dye solvents. Hence, it will deeply stain the cells.

3T3-L1 cells approximately $60 \times 10^4$ cells are seeded for 48-72 hrs to get 70-80% confluence. After 48 hrs 200 µl of AIM (Adipogenesis induction medium) freshly prepared is added. 72 hrs later 200 µl of APM (Adipogenesis progression medium) with the test compounds in different concentrations is added to the wells. The cells are incubated for 48 hrs in a humidified atmosphere (37° C.) of 5% $CO_2$ and 95% air. The supernatant is collected and stored for the estimation of leptin, adiponectin, IL-6 and TNF-alpha. Cells are fixed by adding 100 µl of 10% formalin and ORO staining is done. OD is read at 492 nm microplate reader.

The results are expressed as $IC_{50}$ values using Graph pad prism software. The percentage of inhibition of adipogenesis is calculated as follows.

% Inhibition=$C-T/T*100$

Where C-absorbance of Oil red O in differentiating/undifferentiated cells
T-absorbance of Oil Red O in sample treated differentiating/undifferentiated cells.

TABLE A

| Sample | Percent inhibition at variable concentration | | | | | |
|---|---|---|---|---|---|---|
| | 3.12 µg/ml | 6.25 µg/ml | 12.5 µg/ml | 25 µg/ml | 50 µg/ml | $IC_{50}$ µg/ml |
| Hexane layer | 1.29% | 12.09% | 18.97% | 26.25% | 40.13% | 52.22 |
| Methanol layer | -NIL- | 5.58% | 13.7% | 25.75% | 41.74% | 66.42 |
| $CHCl_3$ layer | -NIL- | 8.91% | 9.58% | 24.21% | 26.66% | — |
| (EtOAc) layer | 18.98% | 26.77% | 53.55% | 73.63% | 88.41% | 9.39 |

The ethyl acetate layer exemplified the best bioactivity in terms of adipogenesis inhibition with an $IC_{50}$ (µg/ml) value of 9.39. This fraction was then subjected to column fractionation to identify the bioactivity (adipogenesis inhibition) biomarker. Column fractionation involved the step of eluting sub fractions of the ethyl acetate layer with increasing polarity of methanol:chloroform mixture. The sub fractions of ethyl acetate layer are labeled as I, II, III and IV are subjected to bioactivity (anti-adipogenesis) evaluation. The essential steps of anti-adipogenic activity evaluation involves the procedure outlined herein above EXAMPLE 1A. The results are summarized herein below in Table B.

TABLE B

| Sample | $IC_{50}$ (µg/ml) |
|---|---|
| Sub fraction I (Non-polar constituents) | 23.21 |
| Sub fraction II (Naturally enriched in piceatannol along with dimers scirpusin A and scirpusin B) | 41.05 |
| Sub fraction III (Naturally enriched in piceatannol dimers scirpusin A and scirpusin B) | 13.31 |
| Sub fraction IV (Naturally enriched in piceatannol dimers scirpusin A and scirpusin B) | 18.75 |

Figure 2:
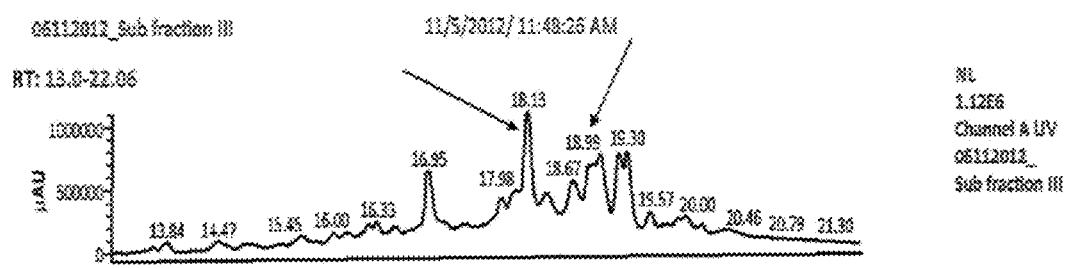
FIGS. 2, 2a, 2b and FIGS. 3, 3a, 3b and 3c show the LC-MS analysis of sub fractions III and IV respectively of the ethyl acetate layer naturally enriched with piceatannol dimers scirpusin A and scirpusin B.
Figure 2A:
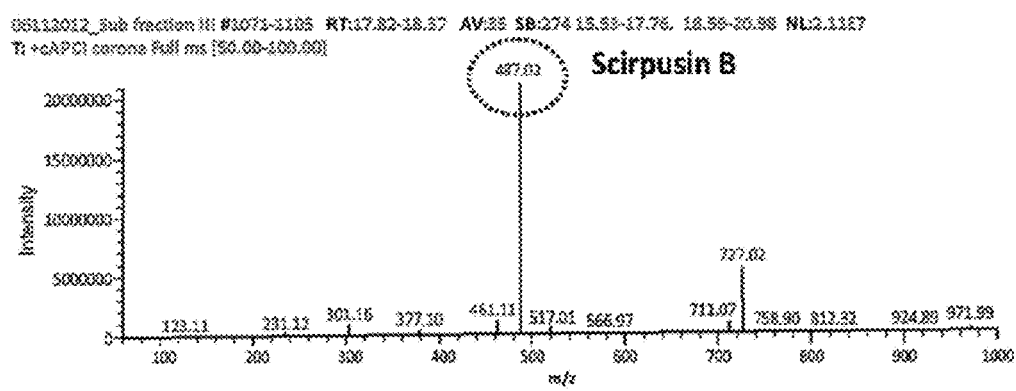
Figure 2B:
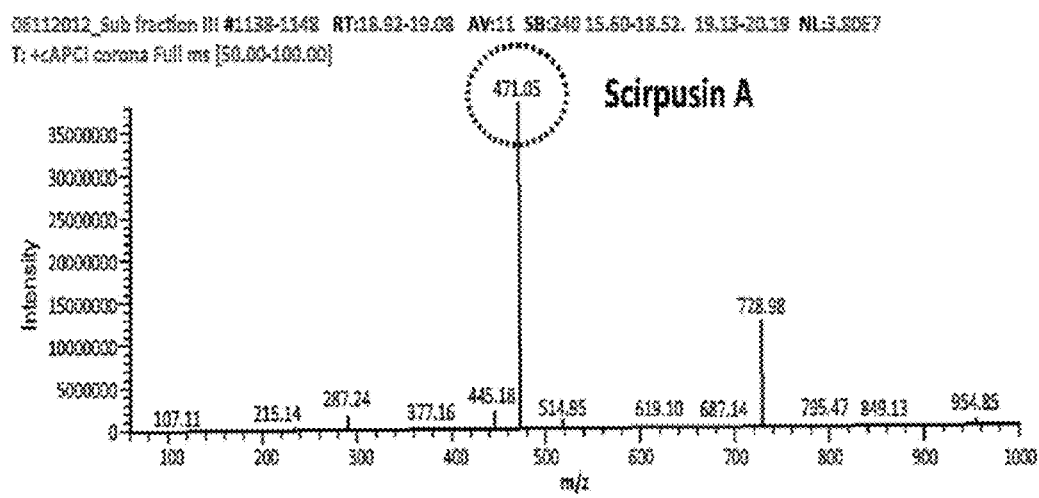
Figure 3:
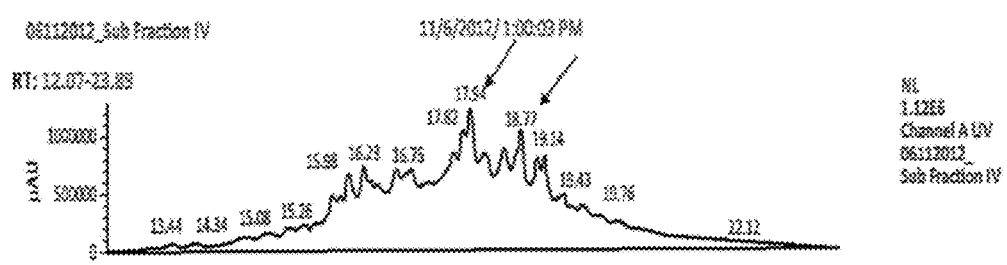
Figure 3A:
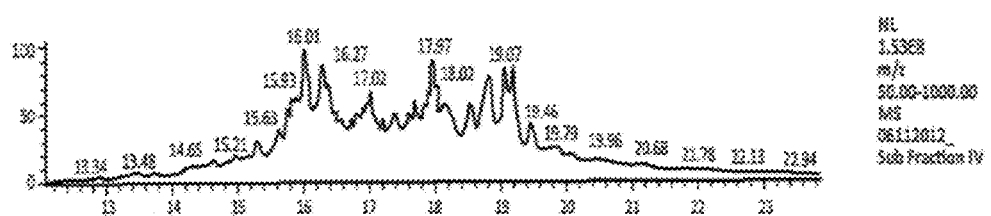
Figure 3B:
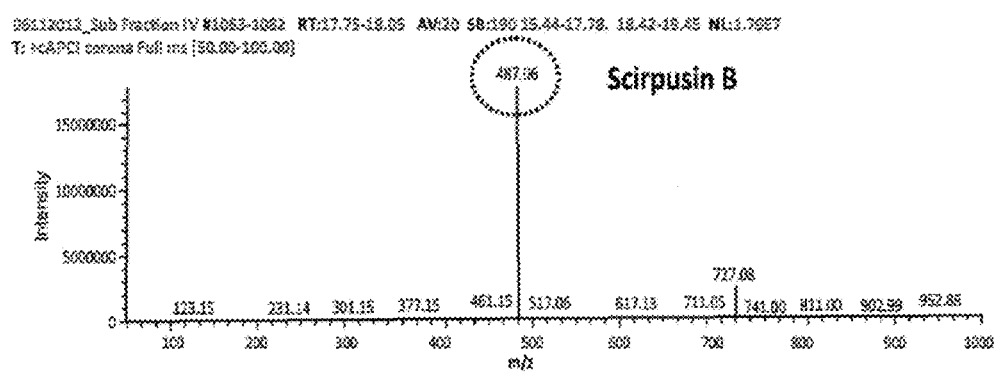
Figure 3C:
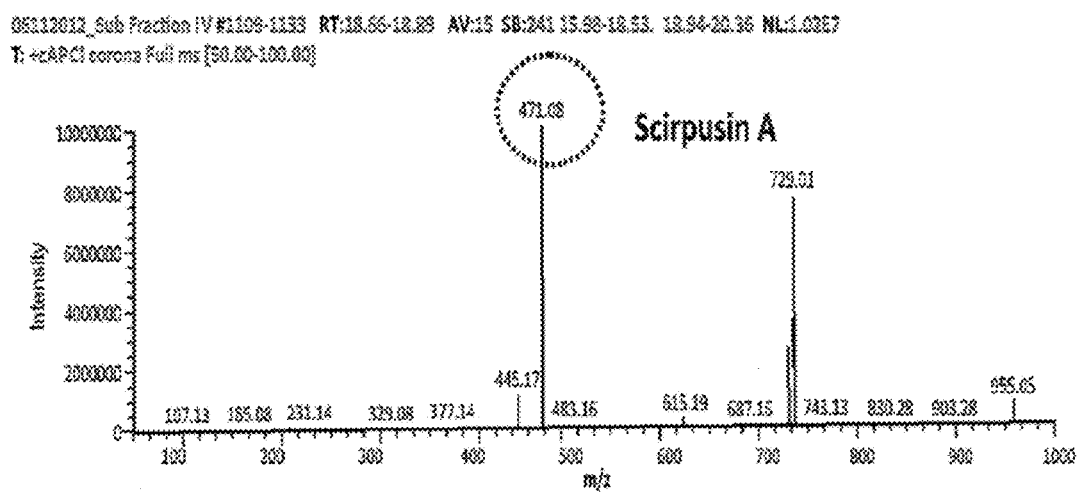

Sub fractions III and IV were then subjected to LC-MS with both fractions being enriched in piceatannol dimers scirpusin A and scirpusin B (FIGS. 2 and 3). The LC-MS/MS analysis was performed on Thermo Electronics Finnigan LCQ Advantage MAX spectrometer using an RP C18 column (250×4.8 mm, 5µ particle size). The system consisted of a Thermo-Finnigan surveyor PDA detector, an LC pump and an autosampler. The Mobile Phase included a Gradient run for 35 minutes with Solvent (A) 0.1% Acetic acid in water and Solvent (B) Acetonitrile. Solvent B concentration increased from 5% during 0-5 minutes, 5-60% during 5-20 minutes, 60-100% during 20-25 minutes, 100-5% during 25-27 minutes and remained constant at 5% during 27-35 minutes. The Stationary phase included Thermo BDS hypersil, C18 Column (Dimension-250 mm×4.6 mm); Flow rate: 1 ml/min; Detection Range: 260 nm.

Ionization parameters: APCI positive mode, Source voltage–4.50 KV. Capillary temperature–225 degrees, Capillary voltage-43.00 V.

Data interpretation: Mass of Scirpusin A is reported to be 470.13. The mass [M+H] observed at 18.77 min in positive ionization mode using the above protocol is 471.08. Mass of Scirpusin B is reported to be 486. The mass [M+H] observed at 17.94 min in positive ionization mode is 487.05.

The first level of confirmation of the presence of dimers of Piceatannol in the Cyperus extract was based on this preliminary information on mass. Scirpusin A Was directly confirmed by direct comparison with an authentic sample of Scirpusin A.

Figure 4:
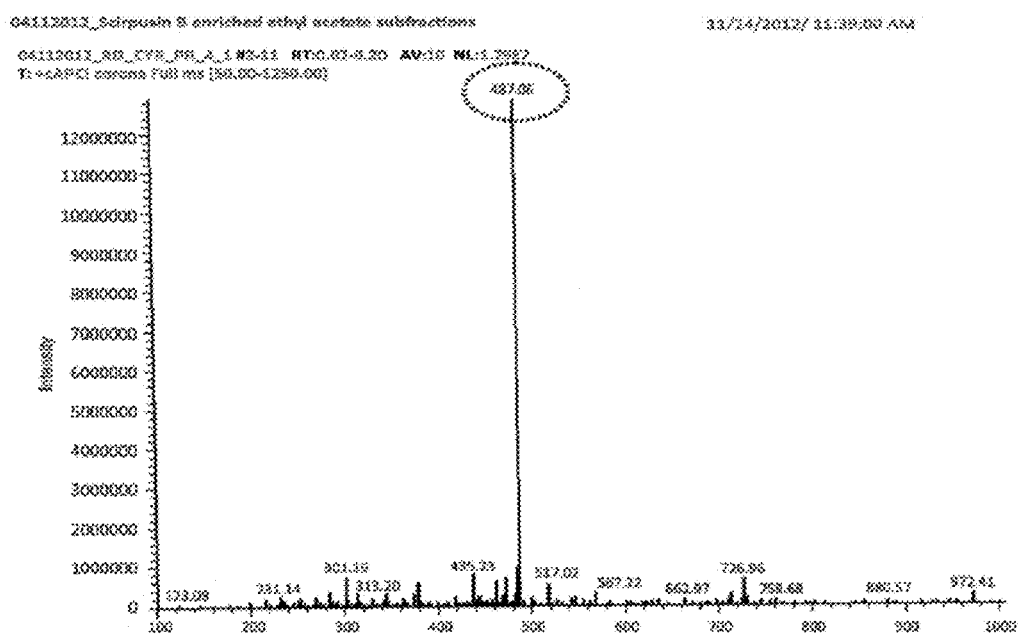
FIGS. 4 and 5 show the data from the HRMS indicating that the [M+H] values obtained therein correspond very well with the structure of the dimer and reported data (Sano et al., 2011) on the same.
Figure 5:
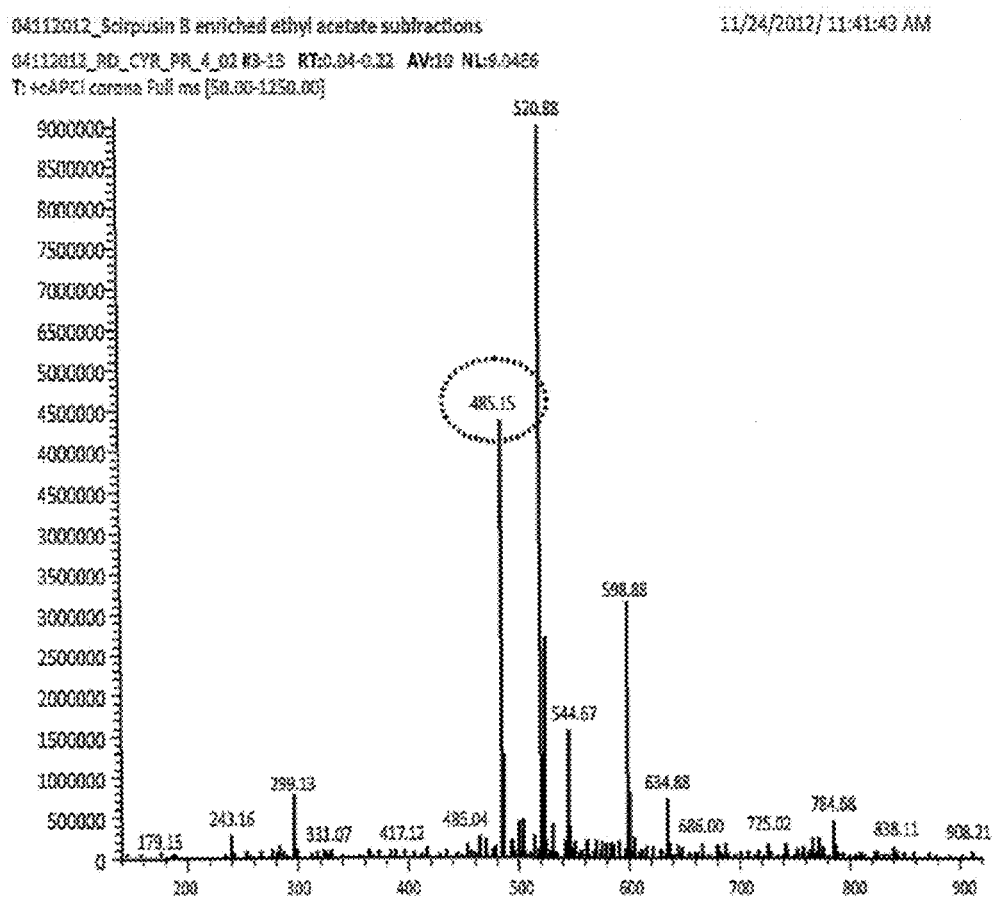

Sub fractions were then subjected through the preparative HPLC to obtain purified dimer scirpusin B which was then studied using the analytical tools High Resolution Mass Spectroscopy (HRMS), liquid chromatography-mass spectrometry (LC-MS/MS) and Nuclear Magnetic Resonance Spectroscopy (NMR) to be confirmed as scirpusin B. Data from the HRMS indicated [M+H]=487.138 which matched very well with the structure of the dimer and reported data (Sano et al., 2011) on the same (FIGS. 4 and 5) and the structure of scirpusin B was also confirmed using cryogenic probe NMR (FIG. 6). The compound was identified after comparison with the data available in literature (Sano et al., 2011), NMR data (CD30D). δ: 55.73, 93.50, 95.39, 100.79, 102.93, 105.87×2, 112.21, 112.63, 114.83, 114.91, 117.03, 118.42, 118.61, 122.17, 129.46, 129.53, 133.53, 135.60, 144.90, 145.01, 145.09, 145.21, 146.27, 158.36, 158.56×2, 161.46. The APT (Attached Proton Test) NMR spectrum obtained at 500 MHz further confirmed the structure of Scirpusin B. Authentic sample of Scirpusin B was also isolated from passion fruits isolated by Sano et. al., 2011 and compared directly with Scirpusin B isolated by us from *Cyperus rotundus* as described above and the identity of HPLC retention times, mass spec data and NMR data corroborated the presence of Scirpusin B in *Cyperus rotundus* in the most convincing way.

Objective of the test: The objective of the study was to evaluate the efficacy of Cypro-AF and Cypro-D1 extracts for anti-obesity effect in C57 mice.

Test System Details:

| | |
|---|---|
| Animal species | Mice |
| Strain | C57 |
| Body weight range | Males: 22-27 g; Females: 20-24 g |
| Age at treatment | 8-10 weeks |
| Number of Groups | 6 groups (One Control; One High fat diet control and Four treatment groups) |
| Number of animals/group | Each group contained 10 animals (5 Males + 5 Females). Female animals used were nulliparous and non-pregnant |
| Total No. of animals | 60 |
| Identification | Cage cards and individual animal ear notching method. |

Test Performance Details

Husbandry

| | |
|---|---|
| Conditions | The animals were housed under standard laboratory conditions, air-conditioned with adequate fresh air supply (Air changes 12-15 per hour), room temperature 22 ± 3 ° C. relative humidity 30-70% with 12 hours light and 12 hours dark cycle. The temperature and relative humidity were recorded once daily. |
| Housing | Individual animals were housed in a standard polypropylene cage (Size: L 290 × B 140 × H 140 mm) with stainless steel mesh top grill having facilities for holding pellet feed and drinking water in water bottle fitted with stainless steel sipper tube. Clean sterilized paddy husk was provided as bedding material. |
| Acclamatization | The animals were acclimatized for 7 days to laboratory conditions and were observed for clinical signs daily. |
| Diet | The animals were fed ad libitum with VRK's "Scientist's Choice" brand Laboratory animal feed manufactured by VRK Nutri-tional Solutions. Bibwewadi—Kondhwa Road, Pune, throughout the acclimatization period. D12450B diet (with 10 kcal % Fat)and D12492 High fat diet (with 60 kcal % Fat) manufactured by Research Diet Inc, USA procured from Indus Marketing, Hyderabad, Andhra Pradesh, INDIA was used for Induction of obesity and Main study. |
| Water | Clean drinking water was provided ad libitum throughout the acclimatization and Obesity induction period. Deep bore-well water passed through reverse osmosis unit was prodded in plastic water bottles with stainless steel sipper tubes. |

Example 2

EFFICACY EVALUATION FOR ANTI-OBESITY EFFECT OF A CYPRO-AF (active ethyl acetate fraction) AND CYPRO-D1 (ethyl acetate sub fraction naturally enriched in piceatannol dimers scirpusin A and scirpusin B) EXTRACTS IN MICE.

Grouping: Grouping of animals was done on the last day of acclimatization by body weight randomization and stratification method. Grouping of animals was done such that body weight variation of animals used does not exceed ±20% of the mean body weight of each group.

Study Design: The animals were divided into 6 groups viz., Group 1, 2, 3, 4, 5 and 6 consisting of 10 animals (5 male and 5 female) each. The group detail, doses and number/sex of animals per group are presented in the following table:

| Group | Treatment | Dose (mg/kg Bwt) | Number of Animals | | Animal Numbers | |
|---|---|---|---|---|---|---|
| | | | Male | Female | Male | Female |
| G1 | Control (with 10 kcal % Fat) | — | 5 | 5 | 1-5 | 31-35 |
| G2 | High fat diet Control (with 60 kcal % Fat) | — | 5 | 5 | 6-10 | 36-40 |
| G3 | CYPRO-AF 50 mg/kg + High fat diet (with 60 kcal % Fat) | 50 | 5 | 5 | 11-15 | 41-45 |
| G4 | CYPRO-AF 100 mg/kg + High fat diet (with 60 kcal % Fat) | 100 | 5 | 5 | 16-20 | 46-50 |

-continued

| Group | Treatment | Dose (mg/kg Bwt) | Number of Animals Male | Number of Animals Female | Animal Numbers Male | Animal Numbers Female |
|---|---|---|---|---|---|---|
| G5 | CYPRO-AF200 mg/kg + High fat diet (with 60 kcal % Fat) | 200 | 5 | 5 | 21-25 | 51-55 |
| G6 | CYPRO-D1 10 mg/kg + High fat diet (with 60 kcal % Fat) | 10 | 5 | 5 | 26-30 | 56-60 |
| | Total: | | 30 | 30 | — | — |
| | Total number of animals: | | | 60 | | |

Formulation Details and Dosage

The test items Cypro-AF and Cypro-DI were dissolved in distilled water for formulating different doses. Freshly formulated test items were administered through oral route by gavage. The volume of dosage per animal as maintained at 10 ml/kg body weight for all the animals throughout the study period. The following table provided details of the test formulation.

| Group | Dose (mg/kg Bwt) | Concentration (mg/ml) | Quantity (mg) | Volume of distilled water (ml) |
|---|---|---|---|---|
| G1 | — | — | — | 4.0 |
| G2 | — | — | — | 4.0 |
| G3 | 50 | 5 | 20 | 4.0 |
| G4 | 100 | 10 | 40 | 4.0 |
| G5 | 200 | 20 | 80 | 4.0 |
| G6 | 10 | 1 | 4 | 4.0 |

Obesity induction: The G1 Control group animals were fed with normal control diet feed D124506 containing 10 kcal % fat and the 32 to 36 group animals were fed with high fat diet feed D12492 containing 60 kcal % fat during the induction of obesity and during main study.

Main Study:

Main study was started after the induction of obesity. The 3 doses of Cypro-AF and 1 dose of Cypro-D1 were administered to animals from Day 28 daily consecutively for a period of 27 days. The feeding of the diets continued in the main study was done in induction of obesity. The G1 Control and G2 High fat diet control group animals administered with distilled water while other groups animals received test items from Day 28 to Day 54 of the study period. The dose volume of administration was maintained according to the weekly body weight of individual animals. The total duration of the study was 61 days (7 days Acclimatization period+27 days Induction of obesity+27 day's Main study).

Observations

The following observations were made for during the study period.

Feed Consumption

Individual animal feed consumption was recorded. Weekly average feed consumption was calculated and recorded.

Body Weight

Individual animal body weights were recorded on the day of receipt on Day 1 and weekly (±1 day) thereafter during the study period.

Clinical Observations

All the animals were clinically observed twice daily during the study period.

Clinical Pathology

At the completion of the study period, blood samples were collected from the animals in tubes containing potassium ethylene di-amide tetra acetic acid (K2-EDTA) anticoagulant for hematology and without anticoagulant for clinical chemistry. The blood samples collected in tubes without anticoagulant were centrifuged at 3000 rpm for 10 minutes to obtain serum. Blood samples were collected humanely from retro-orbital plexus puncture method under mild ether anaesthesia with the help of a fine capillary tube. The following hematology and clinical chemistry parameters were analyzed.

Hematology

The following hematology parameters were estimated using Sysmex, KX-21 (Transasia Bio-Medicals Ltd., India):

| Parameters | Units |
|---|---|
| Hemoglobin (Hb) | g/dL |
| Haematocrit (Ret) | % |
| Erythrocyte Count | $10^6$ cells/µL |
| Total Leukocyte Count | $10^3$ cells/µL |
| Mean corpuscular volume (MCV) | fL |
| Mean corpuscular hemoglobin (MCH) | Pg |
| Mean corpuscular hemoglobin concentration (MCHC) | g/dL |
| Platelet Count | $10^3$ cells/µL |
| Differential Leucocytes Count (DLC) | % |
| Clotting time | secs |

Clinical Chemistry

The following clinical chemistry parameters were analyzed using the "Erba Mannheim Chem Touch analyzer" (Transasia Bio-Medicals Ltd., India) from serum samples.

| Parameters | Units |
|---|---|
| Total Protein | g/dL |
| Albumin | g/dL |
| Glucose | mg/dL |
| Alanine aminotransfese (ALT) | mg/dL |
| Aspartate aminotransferase (AST) | IU/L |
| Triglycerides | IU/L |
| Total Cholesterol | mg/dL |
| High Density lipid (HDL) | mg/dL |
| Very Low density lipid (VLDL) | mg/dL |
| Low density lipid (LOW | mg/dL |

Pathology

After the completion of the study period, on Day 55, all the animals were humanely sacrificed by exposing them to excess carbon-di-oxide in gas chamber and subjected to following external and internal gross necropsy.

Gross Necropsy

The animals were subjected to external and internal gross pathological examinations.

Organ Weights

The following organs from all animals was trimmed of any adherent tissue, as appropriate and weighed wet as soon as possible to avoid drying: Brain, Thymus, Liver, Adrenals, Kidneys (paired organs), spleen, Heart, Ovaries/Testes (paired organs).

Fat Deposits Weights

The following fat deposits from all the animals was collected and weighed.
1. Epididymal Fat
2. Brown Fat
3. Ovarian Fat Statistical Analysis and Report Preparation The raw data obtained from the present study were subjected to computer statistical processing. The computer printout of the data (in the form of appendix) was verified with the original raw data. After verification, the data was subjected to One-way ANOVA (Analysis of Variance) with Dunnett's post test for the data on body weights, hematology and clinical chemistry parameters, organ weights using GraphPad Prism version 5.01, GraphPad Software. All analyses and comparisons will be evaluated at the 95% level of confidence ($P<0.05$), indicated by the designated by the superscripts of a where G1 is compared to G3, G4, G5, and G6 and b where G2 is compared to G3, G4, G5, and G6 throughout the report as stated below: *: Statistically significant ($P<0.05$) wherever applicable.

The data were subjected to one way—ANOVA statistical analysis by comparing the following:

G1 group {Control group (with 10 kcal % Fat)} to G3 group {CYPRO-AF 50 mg/kg+High fat diet (with 60 kcal % Fat)}, G4 group {CYPRO-AF-100 mg/kg+High fat diet (with 60 kcal % Fat)}, G5 group {CYPRO-AF 200 mg/kg+High fat diet (with 60 kcal % Fat) and G6 group {CYPRO-D1 10 mg/kg+High fat diet (with 60 kcal % Fat)} as represented below:

| G1 group | G3 group |
|---|---|
| Control group (with 10 kcal % Fat) | CYPRO-AF 50 mg/kg + High fat diet (with 60 kcal % Fat) |
| | G4 group |
| | CYPRO-AF −100 mg/kg + High fat diet (with 60 kcal % Fat) |
| | G5 group |
| | CYPRO-AF 200 mg/kg + High fat diet (with 60 kcal % Fat) |
| | G6 group |
| | CYPRO-D1 10 mg/kg + High fat diet (with 60 kcal % Fat) |

G2—High fat diet Control (with 60 kcal % Fat) to G3 group {CYPRO-AF 50 mg/kg+High fat diet (with 60 kcal % Fat)}, G4 group {CYPRO-AF-100 mg/kg+High fat diet (with 60 kcal % Fat)}, G5 group {CYPRO-AF 200 mg/kg+High fat diet (with 60 kcal % Fat)} and G6 group {CYPRO-D1 10 mg/kg+High fat diet (with 60 kcal % Fat)} as represented shown below:

| G2 group | G3 group |
|---|---|
| High fat diet Control (with 60 kcal % Fat) | CYPRO-AF 50 mg/kg + High fat diet (with 60 kcal % Fat) |
| | G4 group |
| | CYPRO-AF −100 mg/kg + High fat diet (with 60 kcal % Fat) |
| | G5 group |
| | CYPRO-AF 200 mg/kg + High fat diet (with 60 kcal % Fat) |
| | G6 group |
| | CYPRO-D1 10 mg/kg + High fat diet (with 60 kcal % Fat) |

Results

Feed Consumption

The summary of weekly average feed consumption of male and female animals is presented in TABLE 1 and TABLE 2 respectively. There were no statistical significant differences in the feed consumption of animals during the study period.

TABLE 1

Summary of weekly average feed consumption (g) of male animals
FEED CONSUMPTION (g)

| | | Days | | | | | | | |
|---|---|---|---|---|---|---|---|---|---|
| Group | Treatment | 7 | 14 | 21 | 28 | 35 | 42 | 49 | 54 |
| G1[a] | Control (with to kcal % fat) | 2.80 ± 0.13 | 3.50 ± 0.11 | 4.46 ± 0.10 | 4.55 ± 0.11 | 5.15 ± 0.18 | 4.63 ± 0.23 | 4.82 ± 0.19 | 5.10 ± 0.25 |
| G2[b] | High fat diet Control (with 60 kcal % Fat) | 2.86 ± 0.21 | 3.63 ± 0.15 | 4.38 ± 0.42 | 4.77 ± 0.21 | 5.00 ± 0.27 | 4.89 ± 0.20 | 4.83 ± 0.23 | 4.96 ± 0.14 |
| G3 | CYPRO-AF 50 mg/kg + High fat diet (with 60 kcal % Fat) | 2.79 ± 0.19 | 3.67 ± 0.14 | 4.45 ± 0.10 | 4.75 ± 0.19 | 5.12 ± 0.16 | 4.89 ± 0.35 | 4.96 ± 0.04 | 4.92 ± 0.47 |
| G4 | CYPRO-AF 100 mg/kg + High fat diet (with 60 kcal % Fat) | 2.73 ± 0.16 | 3.64 ± 0.19 | 4.27 ± 0.24 | 4.75 ± 0.18 | 5.12 ± 0.05 | 4.73 ± 0.28 | 4.99 ± 0.16 | 5.15 ± 0.19 |
| G5 | CYPRO-AF 200 mg/kg + High fat diet (with 60 kcal % Fat) | 2.99 ± 0.09 | 3.63 ± 0.15 | 4.41 ± 0.10 | 4.84 ± 0.06 | 5.20 ± 0.13 | 4.89 ± 0.14 | 5.02 ± 0.09 | 5.12 ± 0.12 |

TABLE 1-continued

Summary of weekly average feed consumption (g) of male animals
FEED CONSUMPTION (g)

| Group | Treatment | Days | | | | | | | |
|---|---|---|---|---|---|---|---|---|---|
| | | 7 | 14 | 21 | 28 | 35 | 42 | 49 | 54 |
| G6 | CYPRO-D1 10 mg/kg + High fat diet (with 60 kcal % Fat) | 2.87 ± 0.21 | 3.66 ± 0.18 | 4.34 ± 0.26 | 4.63 ± 0.25 | 5.03 ± 0.26 | 4.91 ± 0.10 | 5.01 ± 0.19 | 5.21 ± 0.25 |

TABLE 2

Summary of weekly average feed consumption (G) of female animals
FEED CONSUMPTION

| Group | Treatment | Days | | | | | | | |
|---|---|---|---|---|---|---|---|---|---|
| | | 7 | 14 | 21 | 28 | 35 | 42 | 49 | 56 |
| G1[a] | Control (with 10 kcal % fat) | 2.90 ± 0.25 | 3.42 ± 0.30 | 3.87 ± 0.31 | 4.40 ± 0.51 | 4.88 ± 0.24 | 4.95 ± 0.15 | 4.54 ± 0.19 | 4.51 ± 0.15 |
| G2[b] | High fat diet Control (with 60 kcal % Fat) | 2.92 ± 0.37 | 3.53 ± 0.25 | 3.54 ± 0.33 | 4.17 ± 0.41 | 4.80 ± 0.36 | 4.59 ± 0.31 | 4.36 ± 0.08 | 4.43 ± 0.13 |
| G3 | CYPRO-AF 50 mg/kg + High fat diet (with 60 kcal % Fat) | 2.77 ± 0.26 | 3.27 ± 0.32 | 3.48 ± 0.22 | 4.27 ± 0.49 | 4.75 ± 0.55 | 5.11 ± 0.09 | 4.42 ± 0.14 | 4.33 ± 0.23 |
| G4 | CYPRO-AF 100 mg/kg + High fat diet (with 60 kcal % Fat) | 2.72 ± 0.15 | 3.40 ± 0.69 | 3.59 ± 0.37 | 4.59 ± 0.27 | 4.55 ± 0.33 | 4.89 ± 0.08 | 4.35 ± 0.21 | 4.38 ± 0.17 |
| G5 | CYPRO-AF 200 mg/kg + High fat diet (with 60 kcal % Fat) | 2.90 ± 0.38 | 3.34 ± 0.30 | 3.56 ± 0.46 | 4.37 ± 0.31 | 4.42 ± 0.39 | 5.02 ± 0.26 | 4.63 ± 0.30 | 4.26 ± 0.12 |
| G6 | CYPRO-DI 10 mg/kg + High fat diet (with 60 kcal % Fat) | 3.08 ± 0.21 | 3.80 ± 0.53 | 3.59 ± 0.31 | 4.65 ± 0.28 | 4.54 ± 0.14 | 5.09 ± 0.19 | 4.56 ± 0.15 | 4.31 ± 0.19 | n = 5;
Values are Mean ± Standard Deviation;
$P > 0.05$

Body Weight

The summary of weekly body weight of male and female animals is presented in Table 3 and Table 4 respectively.

TABLE 3

Summary of body weight (G) of male animals
BODY WEIGHT (g)

| Group | Treatment | Days | | | | |
|---|---|---|---|---|---|---|
| | | 1 | 7 | 14 | 21 | 28 |
| G1[a] | Control (with 10 kcal % fat) | 23.34 ± 1.11 | 23.50 ± 0.93 | 23.88 ± 1.08 | 23.48 ± 0.86 | 25.04 ± 1.05 |
| G2[b] | High fat diet Control (with 60 kcal % Fat) | 23.48 ± 1.06 | 24.10 ± 0.86 | 24.58 ± 1.09 | 26.12 ± 1.12 | 28.48 ± 1.98 |
| G3 | CYPRO-AF 50 mg/kg + High fat diet (with 60 kcal % Fat) | 23.42 ± 1.06 | 24.30 ± 1.63 | 24.90 ± 1.71 | 25.96 ± 1.49 | 27.80 ± 2.84 |

TABLE 3-continued

Summary of body weight (G) of male animals
BODY WEIGHT (g)

| | | | | | | |
|---|---|---|---|---|---|---|
| G4 | CYPRO-AF 100 mg/kg + High fat diet (with 60 kcal % Fat) | 23.24 ± 1.18 | 23.78 ± 1.62 | 24.68 ± 1.48 | 26.14 ± 2.12 | 28.70 ± 1.72 |
| G5 | CYPRO-AF 200 mg/kg + High fat diet (with 60 kcal % Fat) | 23.60 ± 1.03 | 24.32 ± 0.60 | 24.98 ± 1.31 | 26.08 ± 1.01 | 28.90 ± 0.82 |
| G6 | CYPRO-DI 10 mg/kg + High fat diet (with 60 kcal % Fat) | 23.68 ± 1.20 | 24.50 ± 1.19 | 25.24 ± 1.18 | 26.26 ± 1.53 | 29.04 ± 3.11 |

| | Days | | | |
|---|---|---|---|---|
| Group | 35 | 42 | 49 | 55 |
| G1[a] | 26.70 ± 1.40 | 28.62 ± 3.31 | 29.16 ± 3.75 | 31.00 ± 4.12 |
| G2[b] | 30.72 ± 1.72 | 32.50 ± 1.53 | 33.66 ± 1.78 | 35.20 ± 0.95 |
| G3 | 29.48 ± 3.50 | 30.28 ± 3.39 | 30.98 ± 2.95 | 33.34 ± 1.78 |
| G4 | 29.22 ± 3.06 | 30.04 ± 3.38 | 30.00 ± 2.85 | 32.94 ± 2.49 |
| G5 | 30.60 ± 1.65 | 30.50 ± 3.28 | 31.06 ± 3.61 | 33.46 ± 3.40 |
| G6 | 29.62 ± 3.76 | 29.86 ± 2.86 | 30.58 ± 2.63 | 33.38 ± 2.76 | n = 5;
Values are Mean ± Standard Deviation;
$P > 0.05$

TABLE 4

Summary of body weight (G) of female animals
BODY WEIGHT (g)

| | | Days | | | | |
|---|---|---|---|---|---|---|
| Group | Treatment | 1 | 7 | 14 | 21 | 28 |
| G1[a] | Control (with 10 kcal % fat) | 21.08 ± 0.82 | 21.70 ± 0.81 | 22.24 ± 0.26 | 23.12 ± 0.68 | 23.98 ± 1.17 |
| G2[b] | High fat diet Control (with 60 kcal % Fat) | 21.38 ± 1.02 | 22.02 ± 0.67 | 22.20 ± 0.98 | 23.10 ± 0.76 | 25.04 ± 0.34 |
| G3 | CYPRO-AF 50 mg/kg + High fat diet (with 60 kcal % Fat) | 21.14 ± 0.87 | 21.76 ± 0.36 | 22.76 ± 0.68 | 24.30 ± 0.85 | 25.84 ± 0.81 |
| G4 | CYPRO-AF 100 mg/kg + High fat diet (with 60 kcal % Fat) | 21.32 ± 1.03 | 21.62 ± 1.53 | 23.68 ± 1.08 | 25.56 ± 1.19 | 26.32 ± 0.69 |
| G5 | CYPRO-AF 200 mg/kg + High fat diet (with 60 kcal % Fat) | 20.94 ± 0.95 | 21.32 ± 1.18 | 23.14 ± 0.97 | 24.94 ± 1.32 | 26.12 ± 0.98 |
| G6 | CYPRO-D1 10 mg/kg + High fat diet (with 60 kcal % Fat) | 21.34 ± 1.27 | 21.58 ± 0.69 | 23.16 ± 1.08 | 25.46 ± 0.86 | 26.72 ± 0.61 |

| | Days | | | |
|---|---|---|---|---|
| Group | 35 | 42 | 49 | 55 |
| G1[a] | 24.82 ± 2.41 | 25.10 ± 2.59 | 26.12 ± 1.91 | 27.74 ± 1.02 |
| G2[b] | 26.40 ± 0.89 | 28.26 ± 0.78 | 30.70 ± 1.70 | 33.02 ± 1.80 |
| G3 | 25.30 ± 1.35 | 26.62 ± 1.68 | 28.66 ± 1.01 | 30.58 ± 1.76 |
| G4 | 26.30 ± 1.30 | 26.84 ± 2.34 | 28.08 ± 3.07 | 30.30 ± 3.54 |

TABLE 4-continued

Summary of body weight (G) of female animals
BODY WEIGHT (g)

| | | | | |
|---|---|---|---|---|
| G5 | 25.90 ± 1.23 | 26.30 ± 2.04 | 27.62 ± 1.06 | 30.22 ± 1.63 |
| G6 | 26.18 ± 0.98 | 26.08 ± 1.47 | 28.44 ± 1.82 | 29.78 ± 1.74 | n = 5;
Values are Mean ± Standard Deviation;
*Significant difference, $P < 0.05$ In male animals, there was statistical significant increase in mean weekly body weight values of on Day 21 in G3 group {CYPRO-AF-50 mg/kg+High fat diet (with 60 kcal % Fat)}; G4 group {CYPRO-AF-100 mg/kg+High fat diet (with 60 kcal % Fat)}, G5 group {CYPRO-AF-200 mg/kg+High fat diet (with 60 kcal % Fat)} and G6 group {CYPRO-D1-10 mg/kg+High fat diet (with 60 kcal % Fat)} compared to G1 group {Control group (with 10 kcal % Fat)}. These changes were considered to be due to difference in fat content of the feed.

In male animals, there was statistical significant increase in mean weekly body weight values of on Day 28 in G4 group {CYPRO-AF–100 mg/kg+High fat diet (with 60 kcal % Fat)}. G5 group {CYPRO-AF–200 mg/kg+High fat diet (with 60 kcal % Fat)} and G6 group {CYPRO-D1-10 mg/kg+High tat diet (with 60 kcal % Fat)} compared to G1 group {Control group (with 10 kcal % Fat)}. These changes were considered to be due to difference in fat content of the feed.

In male animals, there was decrease in mean weekly body weight values of on Day 35, 42, 49 and 55 in G3 group {CYPRO-AF–50 mg/kg+High fat diet with 60 kcal % Fat)}, G4 group {CYPRO-AF-100 mg/kg+High fat diet (with 60 kcal % Fat)}, G5 group {CYPRO-AF-200 mg/kg+High fat diet (with 60 kcal % Fat)} and G6 group {CYPRO-D1-10 mg/kg+High fat diet (with 60 kcal % Fat)} compared to G1 group {Control group (with 10 kcal % Fat)}. These changes were considered to be due to administration of test items.

In female animals, there was statistical significant increase in mean weekly body weight values of on Day 21 in G4 group {CYPRO-AF-100 mg/kg+High fat diet (with 60 kcal % Fat)}, G5 group {CYPRO-AF-200 mg/kg+High fat diet (with 60 kcal % Fat)} and G6 group {CYPRO-D1-10 mg/kg+High fat diet (with 60 kcal % Fat)} compared to G1 group {Control group (with 10 kcal % Fat)}. These changes were considered to be due to difference in fat content of the feed.

In female animals, there was statistical significant increase in mean weekly body weight values of on Day 28 in G3 group {CYPRO-AF-50 mg/kg+High fat diet (with 60 kcal % Fat)}. G4 group {CYPRO-AF-100 mg/kg+High fat diet (with 60 kcal % Fat)}. G5 group {CYPRO-AF-200 mg/kg+High fat diet (with 60 kcal % Fat)} and G6 group {CYPRO-D1-10 mg/kg+High fat diet (with 60 kcal % Fat)} compared to G1 group {Control group (with 10 kcal % Fat)}. These changes were considered to be due to difference in fat content of the feed.

In female animals, there was decrease in mean weekly body weight values of on Day 35, 42, 49 and 55 in G3 group {CYPRO-AF-50 mg/kg+High fat diet (with 60 kcal % Fat)}. G4 group {CYPRO-AF-100 mg/kg+High fat diet (with 60 kcal % Fat)}. G5 group {CYPRO-AF-200 mg/kg+High fat diet (with 60 kcal % Fat)} and G6 group {CYPRO-D1-10 mg/kg+High fat diet (with 60 kcal % Fat)} compared to G1 group {Control group (with 10 kcal % Fat)} These change were considered to be due to administration of test items.

Clinical Observations

The summary of clinical signs of male and female animals is presented in Table-5 and Table-6 respectively. The animals were found to healthy and normal in health status during the clinical observations during the study period.

TABLE 5

Summary of Clinical Signs Observations in Male Animals

| | | CLINICAL SIGNS OBSERVATIONS | | | | | | | | |
|---|---|---|---|---|---|---|---|---|---|---|
| | | Days | | | | | | | | |
| Group | Treatment | 1 | 2-7 | 8-14 | 15-21 | 22-28 | 29-35 | 36-42 | 43-49 | 50-55 |
| G1[a] | Control (with 10 kcal % fat) | N | N | N | N | N | N | N | N | N |
| G2[b] | High fat diet Control (with 60 kcal % Fat) | N | N | N | N | N | N | N | N | N |
| G3 | CYPRO-AF 50 mg/kg + High fat diet (with 60 kcal % Fat) | N | N | N | N | N | N | N | N | N |
| G4 | CYPRO-AF 100 mg/kg + High fat diet (with 60 kcal % Fat) | N | N | N | N | N | N | N | N | N |
| G5 | CYPRO-AF 200 mg/kg + High fat diet (with 60 kcal % Fat) | N | N | N | N | N | N | N | N | N |

TABLE 5-continued

Summary of Clinical Signs Observations in Male Animals

CLINICAL SIGNS OBSERVATIONS

| Group | Treatment | Days | | | | | | | | |
|---|---|---|---|---|---|---|---|---|---|---|
| | | 1 | 2-7 | 8-14 | 15-21 | 22-28 | 29-35 | 36-42 | 43-49 | 50-55 |
| G6 | CYPRO-DI 10 mg/kg + High fat diet (with 60 kcal % Fat) | N | N | N | N | N | N | N | N | N | n = 5;
N—Normal

TABLE 6

Summary of clinical signs observations of female animals

CLINICAL SIGNS OBSERVATIONS

| Group | Treatment | Days | | | | | | | | |
|---|---|---|---|---|---|---|---|---|---|---|
| | | 1 | 2-7 | 8-14 | 15-21 | 22-28 | 29-35 | 36-42 | 43-49 | 50-55 |
| G1[a] | Control (with 10 kcal % fat) | N | N | N | N | N | N | N | N | N |
| G2[b] | High fat diet Control (with 60 kcal % Fat) | N | N | N | N | N | N | N | N | N |
| G3 | CYPRO-AF 50 mg/kg + High fat diet (with 60 kcal % Fat) | N | N | N | N | N | N | N | N | N |
| G4 | CYPRO-AF 100 mg/kg + High fat diet (with 60 kcal % Fat) | N | N | N | N | N | N | N | N | N |
| G5 | CYPRO-AF 200 mg/kg + High fat diet (with 60 kcal % Fat) | N | N | N | N | N | N | N | N | N |
| G6 | CYPRO-DI 10 mg/kg + High fat diet (with 60 kcal % Fat) | N | N | N | N | N | N | N | N | N | n = 5;
N—Normal

Hematology

The summary of hematological parameters estimations of male and female animals is presented in Table-7 and Table-8 respectively.

TABLE 7

Summary of hematology of male animals

| Group | Treatment | TLC ($10^3$ cells/L) | TEC ($10^6$ cells/L) | Hb g/dL | Hct (%) | MCV (fL) | MCV (pg) |
|---|---|---|---|---|---|---|---|
| G1[a] | Control with 10 kcal % fat | 9.34 ± 1.88 | 9.19 ± 0.48 | 13.04 ± 0.71 | 46.18 ± 3.65 | 50.22 ± 1.63 | |
| G2[b] | High fat Control with 60 kcal % fat | 13.16 ± 7.95 | 9.25 ± 0.80 | 13.30 ± 0.82 | 46.44 ± 3.17 | 50.26 ± 0.86 | |

TABLE 7-continued

Summary of hematology of male animals

| | | | | | | |
|---|---|---|---|---|---|---|
| G3 | CYPRO-AF 50 mg/kg + High fat diet | 7.34 ± 3.51 | 9.48 ± 0.75 | 13.74 ± 1.09 | 48.08 ± 4.30 | 50.72 ± 2.04 |
| G4 | CYPRO-AF 100 mg/kg + High fat diet (with 60 kcal % Fat) | 10.08 ± 7.35 | 9.06 ± 1.19 | 13.34 ± 0.86 | 44.70 ± 5.39 | 49.40 ± 1.31 |
| G5 | CYPRO-AF 200 mg/kg + High fat diet (with 60 kcal % Fat) | 7.44 ± 3.64 | 8.93 ± 1.11 | 13.00 ± 1.82 | 44.84 ± 6.55 | 50.04 ± 1.76 |
| G6 | CYPRO-D1 10 mg/kg + High fat diet (with 60 kcal % Fat) | 9.30 ± 3.51 | 9.57 ± 0.77 | 13.74 ± 0.50 | 47.08 ± 2.16 | 49.32 ± 2.09 |

| Group | MCH (g/dL) | MCHC (g/dL) | Platelet Count ($10^3$ cells/L) |
|---|---|---|---|
| G1[a] | 14.20 ± 0.40 | 28.28 ± 1.11 | 1167.20 ± 139.82 |
| G2[b] | 14.40 ± 0.74 | 28.68 ± 1.27 | 1297.80 ± 176.81 |
| G3 | 14.50 ± 0.46 | 28.58 ± 0.49 | 1297.00 ± 232.56 |
| G4 | 14.86 ± 1.22 | 30.04*[a] ± 1.95 | 1313.20 ± 159.37 |
| G5 | 14.52 ± 0.45 | 29.02 ± 0.33 | 1465.60 ± 168.11 |
| G6 | 14.42 ± 0.75 | 29.20 ± 0.62 | 1389.60 ± 278.21 |

HEMATOLOGY PARAMETERS

| Group | Treatment | Clotting time (sec) | Neutrophils (%) | Lymphocytes (%) | Monocytes (%) | Eosinophils (%) | Basophils (%) |
|---|---|---|---|---|---|---|---|
| G1[a] | Control with 10 kcal % fat | 106.80 ± 10.47 | 21.40 ± 3.21 | 70.00 ± 1.58 | 6.40 ± 1.52 | 0.80 ± 0.45 | 1.60 ± 0.89 |
| G2[b] | High fat Control with 60 kcal % fat | 110.80 ± 14.86 | 20.00 ± 3.94 | 73.00 ± 3.16 | 6.00 ± 1.58 | 0.60 ± 0.55 | 1.00 ± 0.71 |
| G3 | CYPRO-AF 50 mg/kg + High fat diet | 111.20 ± 17.80 | 20.40 ± 2.30 | 71.00 ± 3.08 | 6.60 ± 1.14 | 0.80 ± 0.45 | 1.40 ± 0.89 |
| G4 | CYPRO-AF 100 mg/kg + High fat diet (with 60 kcal % Fat) | 112.20 ± 13.46 | 19.80 ± 3.19 | 72.80 ± 3.42 | 5.80 ± 1.92 | 0.60 ± 0.55 | 1.40 ± 0.55 |
| G5 | CYPRO-AF 200 mg/kg + High fat diet (with 60 kcal % Fat) | 101.00 ± 11.45 | 22.00 ± 2.00 | 68.80 ± 1.64 | 7.00 ± 1.00 | 0.80 ± 0.45 | 1.40 ± 0.55 |
| G6 | CYPRO-D1 10 mg/kg + High fat diet (with 60 kcal % Fat) | 113.20 ± 13.10 | 21.40 ± 2.88 | 70.40 ± 4.16 | 5.80 ± 1.30 | 0.60 ± 0.55 | 1.80 ± 0.84 | n = 5;
Values - Mean ± Standard Deviation;
P > 0.05

TABLE 8

Summary of hematology of female animals

| Group | Treatment | TLC ($10^3$ cells/μL) | TEC ($10^6$ cells/μL) | Hb g/dL | Hct (%) | MCV (fL) | MCH (pg) |
|---|---|---|---|---|---|---|---|
| G1[a] | Control with 10 kcal % fat | 8.74 ± 2.96 | 9.94 ± 0.70 | 13.84 ± 0.81 | 50.06 ± 3.81 | 50.36 ± 1.76 | |

TABLE 8-continued

Summary of hematology of female animals

| Group | Treatment | | | | | |
|---|---|---|---|---|---|---|
| G2[b] | High fate Control with 60 kcal % fat | 8.16 ± 2.55 | 8.97 ± 1.13 | 13.16 ± 1.72 | 45.74 ± 6.65 | 50.88 ± 1.58 |
| G3 | CYPRO-AF 50 mg/kg + High fat diet | 7.06 ± 1.87 | 9.47 ± 0.22 | 14.00 ± 0.50 | 49.84 ± 1.34 | 52.60*a ± 0.31 |
| G4 | CYPRO-AF 100 mg/kg + High fat diet (with 60 kcal % Fat) | 10.56 ± 5.49 | 9.25 ± 0.49 | 13.48 ± 0.73 | 47.50 ± 3.24 | 51.32 ± 1.34 |
| G5 | CYPRO-AF 200 mg/kg + High fat diet (with 60 kcal % Fat) | 7.82 ± 3.18 | 9.73 ± 0.70 | 13.34 ± 0.93 | 49.32 ± 2.70 | 50.74 ± 1.55 |
| G6 | CYPRO-D1 10 mg/kg + High fat diet (with 60 kcal % Fat) | 7.40 ± 2.20 | 9.61 ± 0.52 | 13.82 ± 0.54 | 48.78 ± 1.91 | 50.82 ± 1.13 |

| Group | MCH (g/dL) | MCHC (g/dL) | Platelet Count ($10^3$ cells/f.IL) |
|---|---|---|---|
| G1[a] | 13.94 ± 0.72 | 27.68 ± 1.00 | 1195.40 ± 273.99 |
| G2[b] | 14.66 ± 0.50 | 28.82 ± 0.77 | 1241.80 ± 245.80 |
| G3 | 14.76*a ± 0.29 | 28.10 ± 0.51 | 1144.00 ± 144.65 |
| G4 | 14.58 ± 0.44 | 28.40 ± 0.70 | 1124.00 ± 152.23 |
| G5 | 13.72** ± 0.39 | 27.04**b ± 0.58 | 1109.60 ± 223.81 |
| G6 | 14.40 ± 0.42 | 28.36 ± 0.84 | 1111.60 ± 180.93 |

| Group | Treatment | Clotting time (sec) | Neutrophils (%) | Lymphocytes (%) | Monocyte (%) | Eosinophil (%) | Basophil (%) |
|---|---|---|---|---|---|---|---|
| G1[a] | Control with 10 kcal % fat | 105.60 ± 14.17 | 18.80 ± 3.90 | 74.60 ± 4.45 | 5.40 ± 0.89 | 0.80 ± 0.45 | 1.40 ± 0.89 |
| G2[b] | High fat Control with 60 kcal % fat | 108.60 ± 12.74 | 21.00 ± 3.00 | 72.00 ± 1.87 | 6.20 ± 1.79 | 0.40 ± 0.55 | 1.40 ± 0.55 |
| G3 | CYPRO-AF 50 mg/kg + High fat diet | 117.60 ± 14.79 | 19.60 ± 3.85 | 73.20 ± 4.15 | 5.20 ± 1.10 | 0.80 ± 0.84 | 1.20 ± 0.84 |
| G4 | CYPRO-AF 100 mg/kg + High fat diet (with 60 kcal % Fat) | 104.60 ± 12.05 | 20.40 ± 4.62 | 72.00 ± 4.80 | 6.00 ± 1.58 | 0.80 ± 0.45 | 1.20 ± 0.45 |
| G5 | CYPRO-AF 200 mg/kg + High fat diet (with 60 kcal % Fat) | 111.20 ± 14.25 | 21.60 ± 3.97 | 69.20 ± 3.96 | 7.00 ± 0.71 | 1.00 ± 0.71 | 1.00 ± 0.71 |
| G6 | CYPRO-D1 10 mg/kg + High fat diet (with 60 kcal % Fat) | 109.40 ± 12.54 | 20.60 ± 3.51 | 71.00 ± 2.65 | 6.20 ± 1.48 | 0.80 ± 0.84 | 1.00 ± 0.71 | n = 5;
Values - Mean ± Standard Deviation;
P > 0.05

Hematology Parameters Statistical Analysis Comparison Between G1 to G3, G4, G5, and G6

Mean Corpuscular Hemoglobin Concentration (MCHC)

In male animals, there was statistical significant increase in mean MCHC value of G4 group {CYPRO-AF-100 mg/kg+High fat diet (with 60 kcal % Fat)} compared to G1 group {Control group (with 10 kcal % Fat)}. These changes can be considered as incidental as there was no dose dependent response.

Mean Corpuscular Volume and Mean Corpuscular Hemoglobin

In female animals, there was statistical significant increase in mean MCV and MCH values of G3 group {CYPRO-AF-50 mg/kg+High fat diet (with 60 kcal % Fat)} compared to G1 group {Control group (with 10 kcal % Fat)}. These changes can be considered as incidental as there was no dose dependent response.

Mean Corpuscular Hemoglobin and Mean Corpuscular Hemoglobin Concentration

In female animals, there was statistical significant increase in mean MCH and MCHC values of G5 group {CYPRO-AF-200 mg/kg+High fat diet (with 60 kcal % Fat)} compared to G2 group {High fat diet control group (with 60 kcal % Fat)}. This change can be considered as incidental as there was no dose dependent response.

Clinical Chemistry

The summary of clinical chemistry parameters estimations of male and female animals is presented in Table-9 and Table-10 respectively.

TABLE 9

| Group | Treatment | Total Protein (g/dl) | Albumin (g/dl) | Glucose (mg/dl) | ALT/SGPT (IU/L) | AST/SGOT (IU/L) | Triglyceride (mg/dl) | Total Cholesterol (mg/dl) |
|---|---|---|---|---|---|---|---|---|
| G1[a] | Control (with 10 kcal % Fat) | 6.39 ± 0.39 | 2.73 ± 0.44 | 102.96 ± 48.15 | 58.74 ± 15.21 | 108.69 ± 28.77 | 122.28 ± 36.20 | 86.99 ± 16.72 |
| G2[b] | High fat diet Control (with 60 kcal % Fat) | 7.14 ± 2.31 | 2.70 ± 0.20 | 106.86 ± 34.32 | 55.37 ± 35.47 | 98.57 ± 25.20 | 110.07 ± 19.34 | 128.94 ± 19.01 |
| G3 | CYPRO-AF 50 mg/kg + High fat diet (with 60 kcal % Fat) | 6.15 ± 0.26 | 2.71 ± 0.13 | 93.65 ± 28.95 | 59.42 ± 24.88 | 106.00 ± 23.46 | 94.93 ± 18.82 | 127.31*[a] ± 32.60 |
| G4 | CYPRO-AF 100 mg/kg + High fat diet (with 60 kcal % Fat) | 6.20 ± 0.23 | 2.64 ± 0.23 | 120.34 ± 19.04 | 56.04 ± 25.33 | 84.41 ± 28.56 | 99.65 ± 18.16 | 123.79 ± 25.80 |
| G5 | CYPRO-AF 100 mg/kg + High fat diet (with 60 kcal % Fat) | 6.13 ± 0.61 | 2.57 ± 0.35 | 107.18 ± 37.36 | 42.54 ± 20.06 | 74.28 ± 22.79 | 95.36 ± 18.13 | 107.19 ± 19.26 |
| G6 | CYPRO-D1 10 mg/kg + High fat diet (with 60 kcal % Fat) | 6.50 ± 0.37 | 2.56 ± 0.35 | 103.20 ± 43.46 | 51.31 ± 23.80 | 71.58 ± 20.61 | 97.18 ± 21.58 | 130.72*[a] ± 15.34 |

| Group | Treatment | HDL (mg/dl) | VLDL (mg/dl) | LDL (mg/dl) |
|---|---|---|---|---|
| G1[a] | Control (with 10 kcal % Fat) | 45.12 ± 16.79 | 24.46 ± 7.24 | 45.46 ± 13.24 |
| G2[b] | High fat diet Control (with 60 kcal % Fat) | 85.48 ± 23.04 | 22.01 3.87 | 66.84 ± 17.14 |
| G3 | CYPRO-AF 50 mg/kg + High fat diet (with 60 kcal % Fat) | 40.04***[b] ± 7.49 | 18.99 ± 3.76 | 78.70***[a] ± 14.09 |
| G4 | CYPRO-AF 100 mg/kg + High fat diet (with 60 kcal % Fat) | 55.90**[b] ± 15.76 | 19.93 ± 3.63 | 75.16***[a] ± 17.74 |
| G5 | CYPRO-AF 200 mg/kg + High fat diet (with 60 kcal % Fat) | 20.09**[ab] ± 7.51 | 19.07 ± 3.63 | 59.99 ± 13.73 |
| G6 | CYPRO-D1 10 mg/kg + High fat diet (with 60 kcal % Fat) | 26.82*[b] ± 5.45 | 19.44 ± 4.32 | 81.31*[a] ± 11.64 | n = 5;
Values- Mean ± Standard Deviation;
$P < 0.05$

TABLE 10

CLINICAL CHEMISTRY PARAMETERS IN FEMALE ANIMALS

| Group | Treatment | Total Protein (g/dl) | Albumin (g/dl) | Glucose (mg/dl) | ALT/SGPT (IU/L) | AST/SGOT (IU/L) | Triglyceride (mg/dl) | Total Cholesterol (mg/dl) |
|---|---|---|---|---|---|---|---|---|
| G1[a] | Control (with 10 kcal % Fat) | 6.78 ± 0.36 | 3.11 ± 0.13 | 78.96 ± 18.98 | 40.51 ± 30.20 | 85.76 ± 39.56 | 97.65 ± 36.05 | 75.03 ± 11.41 |
| G2[b] | High fat diet Control (with 60 kcal % Fat) | 6.70 ± 0.72 | 2.86 ± 0.36 | 89.91 ± 26.14 | 35.11 ± 9.73 | 71.58 ± 21.82 | 69.94 ± 35.70 | 97.70 ± 10.92 |
| G3 | CYPRO-AF 50 mg/kg + High fat diet (with 60 kcal % Fat) | 6.23*[a] ± 0.22 | 2.99 ± 0.24 | 85.60 ± 11.61 | 37.14 ± 17.21 | 75.62 ± 21.43 | 34.87***[a] ± 10.72 | 86.45 ± 15.34 |
| G4 | CYPRO-AF 100 mg/kg + High fat diet (with 60 kcal % Fat) | 6.27*[a] ± 0.31 | 3.08 ± 0.24 | 108.98 ± 34.03 | 41.86 ± 14.44 | 66.84 ± 5.55 | 44.60***[a] ± 14.87 | 84.90 ± 12.22 |
| G5 | CYPRO-AF 100 mg/kg + High fat diet (with 60 kcal % Fat) | 6.36 ± 0.37 | 2.99 ± 0.30 | 105.62 ± 27.44 | 35.78 ± 5.12 | 78.49 ± 10.08 | 39.31***[a] ± 8.30 | 105.15*[a] ± 14.39 |
| G6 | CYPRO-D1 10 mg/kg + High fat diet (with 60 kcal % Fat) | 6.73 ± 0.09 | 3.15 ± 0.32 | 110.20 ± 21.29 | 37.81 ± 18.55 | 68.87 ± 19.91 | 29.27***[a] ± 12.83 | 87.39 ± 17.68 |

| Group | Treatment | HDL (mg/dl) | VLDL (mg/dl) | LDL (mg/dl) |
|---|---|---|---|---|
| G1[a] | Control (with 10 kcal % Fat) | 14.70 ± 6.70 | 15.01 ± 2.28 | 42.01 ± 13.27 |
| G2[b] | High fat diet Control (with 60 kcal % Fat) | 20.48 ± 2.54 | 19.54 ± 2.18 | 47.61 ± 14.19 |
| G3 | CYPRO-AF 50 mg/kg + High fat diet (with 60 kcal % Fat) | 16.30**[b] ± 3.89 | 17.29 ± 3.07 | 47.80 ± 11.50 |
| G4 | CYPRO-AF 100 mg/kg + High fat diet (with 60 kcal % Fat) | 11.83***[b] ± 1.87 | 16.98 ± 2.44 | 54.19 ± 5.27 |
| G5 | CYPRO-AF 200 mg/kg + High fat diet (with 60 kcal % Fat) | 12.67***[b] ± 2.97 | 21.03*[a] ± 2.88 | 49.27 ± 4.39 |
| G6 | CYPRO-D1 10 mg/kg + High fat diet (with 60 kcal % Fat) | 9.91***[b] ± 1.90 | 17.48 ± 3.54 | 54.89 ± 13.74 | n = 5;
Values- Mean ± Standard Deviation;
P < 0.05

Clinical Chemistry Parameters Statistical Analysis Comparison Between G1 to Q3, G4, G5, and G6

Total Proteins

In female animals, there was statistical significant decrease in mean Total protein values of G3 group {CYPRO-AF-50 mg/kg+High fat diet (with 60 kcal % Fat)} and G4 group {CYPRO-AF-100 mg/kg+High fat diet (with 60 kcal % Fat)} compared to G1 group {Control group (with 10 kcal % Fat)}. These changes were considered to be due to difference in fat content of the feed.

Triglycerides

In female animals, there was statistical significant decrease in mean Triglyceride values G3 group {CYPRO-AF-50 mg/kg+High fat diet (with 60 kcal % Fat)}. G4 group {CYPRO-AF-100 mg/kg+High fat diet (with 60 kcal % Fat)}. G5 group {CYPRO-AF-200 mg/kg+High fat diet (with 60 kcal % Fat)} and G6 group {CYPRO-D1-10 mg/kg+High tat diet (with 60 kcal % Fat)} compared to G1 group {Control group (with 10 kcal % Fat)}. These change were considered to be due to difference in fat content of the feed.

Total Cholesterol

In male animals, there was statistical significant increase in mean Total Cholesterol value of G3 group {CYPRO-AF-50 mg/kg+High fat diet (with 60 kcal % Fat)} and G6 group {CYPRO-D1 10 mg/kg+High fat diet (with 60 kcal % Fat)} compared to G1 group {Control group (with 10 kcal % Fat)}. These changes were considered to be due to difference in fat content of the feed.

In female animals, there was statistical significant increase in mean Total Cholesterol values of G5 group {CYPRO-AF-200 mg/kg+High fat diet (with 60 kcal % Fat)} compared to G1 group {(Control group (with 10 kcal % Fat)}. This change can be considered due to difference in fat content of the feed.

High Density Lipids

In male animals, there was statistical significant decrease in mean High density lipids value of G5 group {CYPRO-AF-200 mg/kg+High fat diet (with 60 kcal % Fat)} compared to G1 group {Control group (with 10 kcal % Fat)}. This change can be considered due to difference in fat content of the feed.

Low Density Lipids

In male animals, there was statistical significant increase in mean Low density lipids value of G3 group {CYPRO-AF-50 mg/kg+High fat diet (with 60 kcal % Fat)}. G4 group {CYPRO-AF-100 mg/kg+High fat diet (with 60 kcal % Fat)} and G6 group {CYPRO-D1-10 mg/kg+High fat diet (with 60 kcal % Fat)} compared to G1 group {Control group (with 10 kcal % Fat)}. These change were considered to be due to difference in fat content of the feed.

Very Low Density Lipids

In female animals, there was statistical significant increase in mean Very low density lipids value of G5 group {CYPRO-AF-200 mg/kg+High fat diet (with 60 kcal % Fat)} compared to G1 group {Control group (with 10 kcal % Fat)}. This change can be considered due to difference in fat content of the feed.

Clinical Chemistry Parameters Statistical Analysis Comparison Between G2 to G3, G4, G5, and G6

Triglycerides

In male animals, there was decrease in mean Triglycerides values of G3 group {CYPRO-AF 50 mg/kg+High fat diet (with 60 kcal % Fat)}. G4 group {CYPRO-AF-100 Mg/kg+High fat diet (with 60 kcal % Fat)}. G5 group {CYPRO-AF 200 mg/kg+High fat diet (with 60 kcal % Fat)} and G6 group {CYPRO-D1 10 mg/kg+High fat diet (with 60 kcal % Fat)} compared to G2 group High fat diet Control (with 60 kcal % Fat). This decrease in mean Triglycerides values changes could be due the effect of the test items.

In female animals, there was statistical significant decrease in mean Triglycerides values of G6 group {CYPRO-D1 10 mg/kg+High fat diet (with 60 kcal % Fat)} compared to G2 group High fat diet Control (with 60 kcal % Fat). This decrease in mean Triglyceride values changes could be due the effect of the test items.

There was decrease in mean Triglyceride values of G3 group {CYPRO-AF 50 mg/kg+High tat diet (with 60 kcal % Fat)}. G4 group {CYPRO-AF 100 mg/kg+High fat diet (with 60 kcal % Fat)} and G5 group {CYPRO-AF 200 mg/kg+High fat diet (with 60 kcal % Fat)} compared to G2 group High fat diet Control (with 60 kcal % Fat). These decrease in mean Triglyceride values changes could be due the effect of the test items.

Total Cholesterol

In male animals, there was decrease in mean Total Cholesterol values of G3 group {CYPRO-AF 50 mg/kg+High fat diet (with 60 kcal % Fat)}. G4 group {CYPRO-AF-100 mg/kg+High fat diet (with 60 kcal % Fat)} and G5 group {CYPRO-AF 200 mg/kg+High fat diet (with 60 kcal % Fat)}compared to G2 group High fat diet Control (with 60 kcal % Fat). This decrease in mean Total Cholesterol values changes could be due the effect of the test items.

In female animals, there was decrease in mean Total Cholesterol values of G3 group {CYPRO-AF 50 mg/kg+ High fat diet (with 60 kcal % Fat)}. G4 group {CYPRO-AF 100 mg/kg+High fat diet (with 60 kcal % Fat)} and G0 group {CYPRO-D1 10 mg/kg+High fat diet (with 60 kcal % Fat)} compared to G2 group High fat diet Control (with 60 kcal % Fat). This decrease in mean Total Cholesterol values changes could be due the effect of the test items.

High Density Lipids

In male animals, there was statistical significant decrease in mean High density lipids values of G3 group {CYPRO-AF 50 mg/kg+High fat diet (with 60 kcal % Fat)}. G4 group {CYPRO-AF-100 mg/kg+High fat diet (with 60 kcal % Fat)}. G5 group {CYPRO-AF 200 mg/kg+High fat diet (with 60 kcal % Fat)} and G6 group {CYPRO-D1 10 mg/kg+High fat diet (with 60 kcal % Fat)} compared to G2 group High fat diet Control (with 60 kcal % Fat).

The statistical significant decrease in mean High density lipid values changes could be due the effect at the test items.

In female animals, there was statistical significant decrease in mean High density lipids values of G3 group {CYPRO-AF 50 mg/kg+High fat diet (with 60 kcal % Fat)}. G4 group {CYPRO-AF-100 mg/kg+High fat diet (with 60 kcal % Fat)}. G5 group {CYPRO-AF 200 mg/kg+High fat diet (with 60 kcal % Fat)} and G0 group {CYPRO-D1 10 mg/kg+High fat diet (with 60 kcal % Fat)} compared to G2 group High fat diet Control (with 60 kcal Fat). These decreases in mean High density lipid values changes could be due the effect of the test items.

Low Density Lipids

In male animals, there was decrease in mean Low density lipids values of G5 group {CYPRO-AF 200 mg/kg+High fat diet (with 60 kcal % Fat)} compared to G2 group High fat diet Control (with 60 kcal % Fat). This decrease in mean Low density lipid values changes could be due the effect of the test items.

Very Low Density Lipids Values

In male animals, there was decrease in mean Very low density lipids values of G3 group {CYPRO-AF 50 mg/kg+ High fat diet (with 60 kcal % Fat)}, G4 group {CYPRO-AF-100 mg/kg+High fat diet (with 60 kcal % Fat)}, G5 group {CYPRO-AF 200 mg/kg+High fat diet (with 60 kcal % Fat)} and G6 group {CYPRO-D1 10 mg/kg+High fat diet (with 60 kcal % Fat)} compared to G2 group High fat diet Control (with 60 kcal % Fat). This decrease in mean Very low density lipid values changes could be due the effect of the test items.

In female animals, there was marginal decrease in mean Very low density lipids values of G3 group {CYPRO-AF 50 mg/kg+High fat diet (with 60 kcal % Fat)}. G4 group {CYPRO-AF 100 mg/kg+High fat diet (with 60 kcal % Fat)}, and G6 group {CYPRO-D1 10 mg/kg+High fat diet (with 60 kcal % Fat)} compared to G2 group High fat diet Control (with 60 kcal % Fat). These decreases in mean Very low density lipid values changes could be due the effect of the test items.

Conclusion: From the present study, it can be concluded that the test items Cypro-AF and Cypro-D1 had an effect on decreasing parameters such as HDL, Triglycerides, Cholesterol. LDL and VLDL concentrations in high fat diet induced obese male and female C57 animals at 50, 100 and 200 mg/kg body weight of Cypro-AF and 10 mg/kg body weight of Cypro-DI. No significant statistical changes were observed in the organ weights and fat deposits upon necropsy of animals.

Example 3—The Effect of *Cyperus rotundus*, Ethyl Acetate Fraction Comprising Piceatannol and its Dimers Scirpusin A and Scirpusin B for Weight Management in Humans-Efficacy, Safety and Tolerability Studies Study Details Primary objectives included (i) To study the efficacy of *Cyperus rotundus* extract for weight management in obese patients, and (ii) To study the safety and tolerability of *Cyperus rotundas* extract for weight management in obese patients.

Secondary objective included the study of the onset of activity of *Cyperus rotundus* extract in the weight management of obese patients.

Primary outcome measures included, (i) decrease in body weight and body mass index; (ii) decrease in waist circumference and waist:hip ratio (anthropometric measurements), (iii) decrease in Cholesterol, Triglycerides, LDL and VLDL values from baseline, (iv) increase in HDL values from baseline; and (v) Photographic evidence obtained of the subjects on baseline and on last visit while concealing his/her identity.

Secondary outcome measures included assessing the tolerability of the study material ii terms of adverse events and other physical signs or symptoms in the study subjects.

Subject Demographics (Table 11)

TABLE 11

|  | Total |
| --- | --- |
| Age (years) | |
| N | 30 |
| Mean ± SD | 37.5 ± 10.71 |
| Median | 38.0 |
| Height (cm) | |
| N | 30 |

TABLE 11-continued

|  | Total |
| --- | --- |
| Mean ± SD | 1603 ± 10.10 |
| Median | 159.5 |
| Weight (kg) | |
| N | 30 |
| Mean ± SD | 90.1 ± 16.45 |
| Median | 87.1 |
| Body Mass Index (kg/m$^2$) | |
| N | 30 |
| Mean ± SD | 34.57 ± 3.84 |
| Median | 33.9 |
| Gender [n (%)] | |
| Male | 8 (26.67) |
| Female | 22 (73.33) |

Illustrative Formulations used in the Human Study (Tables 12 and 13)

TABLE 12

| | Ingredients (Active Study Material) | Weight (mg) |
| --- | --- | --- |
| 1 | *Cyperus rotundus* extract (5% of total Stilbenes)—Extract comprising Piceatannol. Scitpusin A and Scirpusin B | 525 |
| 2 | Dibasic calcium phosphate | 30 |
| 3 | Magnesium stearate | 5 |

TABLE 13

| Ingredients (Placebo) | Weight (mg) |
| --- | --- |
| Microcrystalline cellulose | 560 mg |

The active study material and placebo described herein above were formulated as size "00" brown/brown hard gelatin capsules with a fill weight of 560 mg. Being a double blinded study, both active study material capsule and placebo capsule were identical in all physical aspects like size, shape and weight. A randomly selected batch of active study material when analyzed showed 36.18 mg of Piceatannol and Scirpusin B on an average per capsule. In more illustrative embodiments, the illustrative formulations that comprise *Cyperus rotundus* extract standardised to contain greater than 3% of total stilbenes including piceatannol, scirpusin A and scirpusin B. In the illustrative example, enunciated in Table 12, *Cyperus rotundus* extract standardised to contain 5% of total stilbenes including piceatannol, scirpusin A and scirpusin B has been presented.

The trial was conducted in Government Ayurveda Medical College, Mysore, India. The study was initialed only after obtaining a written favorable opinion from the institutional ethical committee. No further changes or amendments were made to the approved protocol during the course of the study. The trial was conducted in accordance with the principles enunciated in the Declaration of Helsinki (Edinburgh, 2000) and the ICH harmonized tripartite guideline on Good Clinical Practice (GCP). Written and oral information about the study in a language understandable by the subject was provided to all subjects.

This randomized, double blind, parallel group, placebo controlled, study had total 5 visits to the clinical site by the study subjects, besides screening visit. The schedule of assessments is represented in Table 14.

TABLE 14

| Assessments | Day −3 | Day 0 | 15 | 30 | 60 | 90 | At least 15 days from last visit |
|---|---|---|---|---|---|---|---|
| Written Informed Consent | X | | | | | | |
| Inclusion and Exclusion Criteria | | X | | | | | |
| Randomization | | X | | | | | |
| IP dispensing | | X | X | X | X | | |
| Urine Pregnancy Test for Women [a] | X | | | | X | X | |
| Demographics | X | | X | X | X | X | |
| Anthropometric measurements | | X | X | X | X | X | |
| Physical Examination | X | | X | X | X | X | |
| Medical History | X | | | | | | |
| Medication History | X | | | | | | |
| Treatment History | X | | | | | | |
| Co-Morbid Conditions | X | | | | | | |
| Hematology | X | | | | | X | |
| Biochemistry | X | | | | | X | |
| Virology | X | | | | | | |
| QOL questionnaires | | X | | | | X | |
| Vital Signs | X | X | X | X | X | X | |
| Adverse Event & overall well being | | X | X | X | X | X | X |
| Concomitant Medication | | X | X | X | X | X | X |

Subjects were included in the study if indicated "Yes" to all of the inclusion criteria and "No" to any of the exclusion criteria. Inclusion Criteria: 1) Male and/or female patients 2) Age between 20 to 65 years 3) Elevated levels of Serum Cholesterol more than 200 mg per dL 4) Elevated Serum Triglycerides more than 150 mg per dL 5) Elevated Serum LDL more than 130 mg per dL and or Elevated Serum VLDL more than 40 mg per dL 6) BMI between ≥30 to 40 Kg/m2 7) Willing to come for regular follow-up visits 8) Able to give written informed consent. Exclusion Criteria: 1) Intake of over the counter weight loss agents, centrally acting appetite suppressants in the previous six months, 2) Pathophysioiogic/genetic syndromes associated with obesity (Cushing's syndrome, Turner's syndrome, Prader with syndrome), 3) Patients with evidence of malignancy 4) Patients with poorly controlled Diabetes Mellitus (HbA1c>10%), 5) Patients with poorly controlled Hypertension (>160/100 mm Hg), 6) Patients on prolonged (>6 weeks) medication with corticosteroids, antidepressants, anti-cholinergics, etc. or any other drugs that may have an influence on the outcome of the study, 7) Patients suffering from major systemic illness necessitating long term drug treatment (Rheumatoid arthritis, Rhizomeculosis, Psycho-Neuro-Endocrine disorders, etc.), 8) Patients who have a past history of Atrial Fibrillation, Acute Coronary Syndrome, Myocardial Infarction, Stroke or Severe Arrhythmia in the last 6 months, 9) Symptomatic patient with clinical evidence of Heart failure, 10) Patients with concurrent serious hepatic disorder (defined as Aspartate Amino Transferase (AST) and or Alanine Amino Transferase (ALT), Total Bilirubin, 11) Alkaline Phosphatase (ALP)>2.5 times upper normal limit) or Renal Disorders (defined as S. Creatinine>1.2 mg/dL). Severe Pulmonary Dysfunction (uncontrolled Bronchial Asthma and/or Chronic Obstructive Pulmonary Disease [COPD]), or any other condition that may jeopardize the study, 12) History of HIV and other viral infections, 13) Alcoholics and/or drug abusers, 14) Prior surgical therapy for obesity, 15) History of hypersensitivity to any of the herbal extracts or dietary supplement, 16) Pregnant lactating woman, 17) Patients who have completed participation in any other clinical trial during the past six (06) months, 18) Any other condition which the Principal Investigator thinks may jeopardize the study.

Randomization, Treatment Allocation and Study Procedures

As this was a pilot study, no formal sample size was calculated. Each participant was assigned a 6-digit randomization code and the investigational products were dispensed by site personnel as per the randomization code list generated by an independent statistician. Double blinding to the investigational products was accomplished by an independent blinding of the dosing kits and therefore both clinical site staff and participants remained blinded to the treatment received throughout the study duration. Subject demographics was captured for all enrolled subjects on the screening visit (Table 11). Obese patients not on any other treatment in the previous 3 months were enrolled into the study. All enrolled subjects were advised to adhere to the schedule of events (Table 14) of the study. Enrolled subjects were allotted between active and placebo groups in 1.1 ratio. Subjects used this product on an outpatient basis and were asked to self administer two gelatin capsules per day (each weighing 560 mg) either active or placebo, at least 30 minutes before a meal, preferably in the morning and evening as a dietary ingredient for a period of 90 days. They were scheduled to return for clinical evaluations on day 15, day 30, day 60 and day 90. Telephonic follow up was made at least 15 days from the last scheduled visit on subjects well being. Daily diet and physical activities were recorded in the patient diaries provided to them on visit 1. The same was checked and verified at subsequent visits by the investigators. Compliance with study supplement was reviewed at each visit by examination of the returned supplements. Data collection during this clinical study and statistical analysis were performed by separate functional groups a certified, independent statistician respectively. No changes or amendments were made to the approved protocol after the trial commenced and no interim analysis was done during the study period. The safety outcomes were measured by: 1) Physical Examination and Vitals, 2) Assessment of reported adverse events (AEs), if any, 2) Adverse events, if any. The efficacy outcomes were measured by 1) weight. BMI, waist circumference, hip circumference and waist hip ratio.

Statistical Analysis

Statistical Analysis Software (SAS) of version 9.2 software was used for data analysis for the human clinical study. Paired 't' test, Analysis of Covariance (ANCOVA) and Wilcoxon signed rank sum test were used for appropriate data set variables to reach the best possible statistical conclusion between the active and placebo receiving groups A 'p' value<0.05 was considered as statistically significant. The baseline descriptors were summarized as means and standard deviations for continuous variables and as frequencies and percentages for categorical variables. Last Observation Carry Forward (LOCF), the intent to treat method was followed for efficacy evaluations of subjects.

Results

None of the enrolled subjects had abnormal medical history or abnormal physical findings observed on the screening visit or during the study visits. No statistically significant changes in vitals observed between the treatment groups on any of the study visits. Out of 30 randomized patients, 26 completed the study. The ratio of male to female subjects completed all study visits is 7:19, 3 females dropped out of study at various time points, wherein an analysis at the end of the study revealed that 3 out of 4 dropped out subjects were receiving placebo. The percentage of treatment compliance for 26 patients who completed the study was good. The least was 87.22% and maximum was 100% treatment compliance by 19 study subjects. The trial was not prematurely terminated and was stopped only after reaching the target sample size of 30. No statistically significant changes in the vitals (Table 15) and no clinically significant abnormal lab values (Tables 16 and 17) were observed from the baseline to final visits and between the treatment groups There was single AE reported during the entire study period, and as per the investigator's opinion, the event was 'unrelated' to the study product. There were no serious adverse events or significant adverse events noticed in this study. Efficacy analysis of these primary parameters reveals that weight. BMI and waist circumference reached statistical significance between the two treatment groups by end of the study, while the other two parameters (hip circumference and waist hip ratio) did not show any significance between the two treatment groups. Few biochemical assessments (Table 18) like total cholesterol, triglycerides, low density lipoproteins, high density lipoproteins and very low density lipoproteins were found to be statistically significant (p<0.01) when compared between the two treatment group patients (Table 18). Photographs of subjects before and after the study duration clearly indicate the efficacy of the product.

TABLE 15

| Vital Parameter | Product | Baseline | Final | p-value* |
|---|---|---|---|---|
| Systolic Blood Pressure (mmHg) | Placebo | 128.0 | 126.7 | 0.1661 |
| | Active | 134.7 | 133.6 | 0.3356 |
| Diastolic Blood Pressure (mmHg) | Placebo | 82.7 | 81.7 | 0.3388 |
| | Active | 86.0 | 85.7 | — |
| Heart Rate (Beats per minute) | Placebo | 73.9 | 73.8 | 0.1661 |
| | Active | 72.8 | 72.6 | — |
| Pulse Rate (Beats per minute) | Placebo | 67.3 | 67.0 | — |
| | Active | 68.1 | 68.1 | — |
| Respiratory Rate (Breaths per minute) | Placebo | 14.0 | 14.0 | — |
| | Active | 13.7 | 13.7 | — |
| Oral Temperature (degrees Fahrenheit) | Placebo | 98.6 | 98.6 | — |
| | Active | 98.4 | 98.5 | — |

Values expressed as mean ± S.E
*p-value is estimated from paired t-test

TABLE 16

| Lab Parameter | Visit | Placebo | Active | Normal range |
|---|---|---|---|---|
| Alanine aminotransferase (IU/L) | Baseline | 30.5 ± 16.81 | 34.7 ± 24.62 | 0 to 41 |
| | Final Visit | 34.3 ± 11.87 | 30.3 ± 8.63 | |
| Alkaline phosphatase (IU/L) | Baseline | 79.5 ± 16.25 | 77.4 ± 23.25 | 53 to 128 |
| | Final Visit | 101.8 ± 32.50 | 106.5 ± 24.26 | |
| Aspartate aminotransferase (IU/L) | Baseline | 36.9 ± 20.32 | 33.1 ± 32.16 | 0 to 40 |
| | Final Visit | 38.6 ± 22.40 | 30.2 ± 10.44 | |
| Chloride | Baseline | −1.0 ± 0.00 | −1.0 ± 0.00 | |
| | Final Visit | 100.2 ± 2.08 | 100.2 ± 1.72 | |
| Potassium | Baseline | −1.0 ± 0.00 | −1.0 ± 0.00 | |
| | Final Visit | 4.2 ± 0.35 | 4.4 ± 0.33 | |
| Serum Creatinine (mg %) | Baseline | 0.9 ± 0.08 | 0.9 ± 0.13 | 0.6 to 1.4 |
| | Final Visit | 0.9 ± 0.13 | 0.8 ± 0.13 | |
| Sodium (mg/L) | Baseline | −1.0 ± 0.00 | −1.0 ± 0.00 | 136 to 145 |
| | Final Visit | 138.3 ± 2.15 | 139.5 ± 2.44 | |
| Total Bilirubin (mg/dL) | Baseline | 0.8 ± 0.19 | 1.2 ± 1.62 | 0.1 to 1.2 |
| | Final Visit | 0.8 ± 0.22 | 0.8 ± 0.24 | |
| Uric Acid | Baseline | −1.0 ± 0.00 | −1.0 ± 0.00 | |
| | Final Visit | 4.4 ± 0.58 | 4.9 ± 0.73 | |
| Blood urea nitrogen (mg/dL) | Baseline | 12.3 ± 3.38 | 10.7 ± 1.66 | 5.0 to 24 |
| | Final Visit | 11.1 ± 2.69 | 10.9 ± 1.85 | |
| Fasting blood sugar (mg/dL) | Baseline | 99.1 ± 2.54 | 106.2 ± 3.89 | 70 to 110 |
| | Final Visit | 104.2 ± 2.99 | 120.4 ± 9.48 | |

Values expressed as mean ± S.D

TABLE 17

| Lab Parameter | Visit | Placebo | Active | Normal range |
|---|---|---|---|---|
| Erythrocyte Count (RBC) (*$10^6$ cells) | Baseline | 4.3 ± 0.47 | 4.4 ± 0.34 | 4.0 to 6.5 |
| | Final Visit | 4.3 ± 0.54 | 4.4 ± 0.33 | |
| Haematocrit (%) | Baseline | 37.5 ± 5.37 | 36.7 ± 5.80 | 40 to 50 |
| | Final Visit | 39.5 ± 6.32 | 37.2 ± 3.11 | |

TABLE 17-continued

| Lab Parameter | Visit | Placebo | Active | Normal range |
|---|---|---|---|---|
| Haemoglobin | Baseline | 12.8 ± 2.03 | 12.1 ± 1.77 | 11 to 16 |
| (gm %) | Final Visit | 13.6 ± 2.29 | 12.4 ± 1.57 | |
| Luekocyte Count | Baseline | 8893.3 ± 2189.09 | 9980.0 ± 1607.22 | |
| (WBC)(Cells/cu. mm) | Final Visit | 9033.3 ± 2371.55 | 9330.8 ± 2146.46 | 4000 to 11000 |
| Platelet Count | Baseline | 4.0 ± 0.70 | 4.2 ± 0.72 | 1.5 to 4.5 |
| (*10$_5$ per cu. mm) | Final Visit | 3.7 ± 0.90 | 3.8 ± 0.79 | |
| Lymphocytes (%) | Baseline | 31 ± 0.06 | 30 ± 0.06 | 25 to 40 |
| | Final Visit | 29 ± 0.06 | 30 ± 0.06 | |
| Monocytes (%) | Baseline | 0.0 ± 0.00 | 0.0 ± 0.00 | 0 to 10 |
| | Final Visit | 0.0 ± 0.00 | 0.0 ± 0.00 | |
| Neutrophils (%) | Baseline | 59 ± 0.05 | 61 ± 0.06 | 40 to 75 |
| | Final Visit | 61 ± 0.06 | 63 ± 0.07 | |
| Basophils (%) | Baseline | 0.0 ± 0.00 | 0.0 ± 0.00 | 0 to 1 |
| | Final Visit | 0.0 ± 0.00 | 0.0 ± 0.00 | |
| Eosinpophits (%) | Baseline | 0.0 ± 0.00 | 0.0 ± 0.00 | 0 to 7 |
| | Final Visit | 0.0 ± 0.00 | 0.0 ± 0.00 | |

Values expressed as mean ± S.D

TABLE 18

| Parameter | Placebo | | Active | | p-value | 95% CI |
|---|---|---|---|---|---|---|
| | Baseline | Visit5 | Baseline | Visit5 | | |
| Total Cholestrol (mg/dL) | 218.5 ± 13.17 | 218.8 ± 14.29 | 219.4 ± 16.29 | 182.4 ± 10.27 | <0.01 | −43.83, −23.84 |
| Triglycerides (mg/dL) | 182.3 ± 17.28 | 181.8 ± 16.88 | 182.3 ± 30.84 | 171.2 ± 24.93 | 0.0011 | −16.40, −4.724 |
| Low density Lipo protein (mg/dL) | 168.8 ± 19.13 | 167.9 ± 17.78 | 173.5 ± 19.89 | 159.3 ± 19.61 | <0.01 | −17.34, −8.542 |
| High density Lipo protein (mg/dL) | 42.4 ± 2.43 | 42.8 ± 2.72 | 40.9 ± 3.70 | 64.4 ± 3.65 | <0.01 | 19.468, 24.759 |
| Very Low density Lipo protein (mg/dL) | 46.8 ± 10.19 | 44.4 ± 13.30 | 47.9 ± 11.39 | 33.9 ± 7.21 | 0.0018 | −17.82, −4.641 |

*The subjects who completed the final visit were considered for this analysis

In another most preferred embodiment, the present invention relates to a method of reducing obesity in humans, said method comprising step of administering to said humans orally twice a day, composition comprising the ethyl acetate fraction of the extract of *Cyperus rotundus* rhizomes standardized to contain 5% of total stilbenes to achieve the effects of reduction in body weight, body mass index and waist circumference. In a more specific embodiment, the composition comprising the ethyl acetate fraction of the extract of *Cyperus rotundus* rhizomes standardized to contain 5% of total stilbenes consists essentially of piceatannol and dimers thereof. In still more specific embodiments, the composition comprising the ethyl acetate fraction of the extract of *Cyperus rotundus* rhizomes standardized to contain 5% of total stilbenes consists essentially of piceatannol, scirpusin A and scirpusin B.

In yet another most preferred embodiment, the present invention relates to a method of treating hypercholesterolemia in humans, said method comprising step of administering to said humans orally twice a day, composition comprising the ethyl acetate fraction of the extract of *Cyperus rotundus* rhizomes standardized to contain 5% of total stilbenes to achieve the effects of (a) reduction in the systemic levels of total cholesterol, Low Density Lipoproteins (LDL), Very Low Density Lipoproteins (VLDL) and serum triglycerides and (b) enhancement in the systemic levels of High Density Lipoproteins (HDL). In a more specific embodiment, the composition comprising the ethyl acetate fraction of the extract of *Cyperus rotundus* rhizomes standardized to contain 5% of total stilbenes consists essentially of piceatannol and its dimers. In still more specific embodiments, the composition comprising the ethyl acetate fraction of the extract of *Cyperus rotundus* rhizomes standardized to contain 5% of total stilbenes consists essentially of piceatannol, scirpusin A and scirpusin B.

As additional illustrative embodiment, the present invention relates to a method of reducing obesity in humans, said method comprising step of administering to said humans orally twice a day, composition comprising the ethyl acetate fraction of the extract of *Cyperus rotundus* rhizomes standardized to contain greater than 3% of total stilbenes to achieve the effects of reduction in body weight, body mass index and waist circumference. In a more specific embodiment, the composition comprising the ethyl acetate fraction of the extract of *Cyperus rotundas* rhizomes standardized to contain greater than 3% of total stilbenes consists essentially of piceatannol and dialers thereof. In still more specific embodiments, the composition comprising the ethyl acetate fraction of the extract of *Cyperus rotundas* rhizomes standardized to contain greater than 3% of total stilbenes consists essentially of piceatannol, scirpusin A and scirpusin B.

As further additional illustrative example, the present invention also relates to a method of treating hypercholesterolemia in humans, said method comprising step of administering to said humans orally twice a day, composition comprising the ethyl acetate fraction of the extract of *Cyperus rotundus* rhizomes standardized to contain greater than 3% of total stilbenes to achieve the effects of (a) reduction in the systemic levels of total cholesterol, Low Density Lipoproteins (LDL), Very Low Density Lipoproteins (VLDL) and serum triglycerides and (b) enhancement in the systemic levels of High Density Lipoproteins (HDL).

In a more specific embodiment, the composition comprising the ethyl acetate fraction of the extract of *Cyperus rotundas* rhizomes standardized to contain greater than 3% of total stilbenes consists essentially of piceatannol and its dimers. In still more specific embodiments, the composition comprising the ethyl acetate fraction of the extract of *Cyperus rotundas* rhizomes standardized to contain greater than 3% of total stilbenes consists essentially of piceatannol, scirpusin A and scirpusin B.

While the invention has been described with respect to a preferred embodiment it is to be clearly understood by those skilled in the art that the invention is not limited thereto. Rather, scope of the invention is to be interpreted only in conjunction with the appended claims.

We claim:

1. A method of reducing obesity in a human, said method comprising
   administering to said human orally twice a day a composition derived from bioactivity guided fractionation of ethyl acetate extract of the rhizomes of *Cyperus rotundus*,
   wherein:
   said composition is standardized to contain 5% w/w of total stilbenes to achieve the effects of reduction in body weight, body mass index, and waist circumference, and
   the composition consists essentially of a combination of piceatannol, scirpusin B, and scirpusin A.

2. A method of reducing obesity in a human, said method comprising
   administering to said human orally twice a day a composition derived from bioactivity guided fractionation of ethyl acetate extract of the rhizomes of *Cyperus rotundus*,
   wherein:
   said composition is standardized to contain greater than 3% w/w of total stilbenes to achieve the effects of reduction in body weight, body mass index and waist circumference, and
   the composition consists essentially of a combination of piceatannol, scirpusin B, and scirpusin A.

* * * * *